(12) United States Patent
Kato et al.

(10) Patent No.: US 6,872,182 B2
(45) Date of Patent: Mar. 29, 2005

(54) ELECTRONIC SPHYGMOMANOMETER

(75) Inventors: Hiroyuki Kato, Kyoto (JP); Takahide Tanaka, Kyoto (JP); Yoshihiko Sano, Kyoto (JP); Shojiro Oku, Kyoto (JP)

(73) Assignee: Omron Corporation, Kyoto (JP)

(*) Notice: Subject to any disclaimer, the term of this patent is extended or adjusted under 35 U.S.C. 154(b) by 75 days.

(21) Appl. No.: 10/169,947

(22) PCT Filed: Nov. 14, 2001

(86) PCT No.: PCT/JP01/09965
§ 371 (c)(1),
(2), (4) Date: Nov. 4, 2002

(87) PCT Pub. No.: WO02/39893
PCT Pub. Date: May 23, 2002

(65) Prior Publication Data
US 2004/0077958 A1 Apr. 22, 2004

(30) Foreign Application Priority Data
Nov. 20, 2000 (JP) .................... 2000-346076
Feb. 5, 2001 (JP) ..................... 2001-28334

(51) Int. Cl.[7] .................................. A61B 5/02
(52) U.S. Cl. ....................................... 600/490
(58) Field of Search ................. 600/490–501, 600/481, 485

(56) References Cited

U.S. PATENT DOCUMENTS

| | | | | |
|---|---|---|---|---|
| 4,105,021 A | * | 8/1978 | Williams et al. | 600/496 |
| 4,779,626 A | * | 10/1988 | Peel et al. | 600/488 |
| 4,998,534 A | * | 3/1991 | Claxton et al. | 600/483 |
| 5,111,826 A | | 5/1992 | Nasiff | |
| 5,778,879 A | * | 7/1998 | Ota et al. | 600/485 |
| 6,547,741 B2 | * | 4/2003 | Mori et al. | 600/490 |
| 6,712,769 B2 | * | 3/2004 | Freund et al. | 600/503 |

FOREIGN PATENT DOCUMENTS

| | | | |
|---|---|---|---|
| EP | 0 423 553 | 4/1991 | |
| EP | 1254629 A1 | * 11/2002 | ........... A61B/5/022 |
| JP | 3-231630 | 10/1991 | |
| JP | 08000580 A | * 1/1996 | ........... A61B/5/022 |
| WO | WO 98/53734 | 12/1998 | |
| WO | WO 99/33395 | 7/1999 | |

OTHER PUBLICATIONS

JP 08000580 A, Kami et al, SPHYGMOMANOMETER, Jan. 9, 1996, (TRANSLATION).*
Tanaka et al. "New Protable Instrument for Long–Term Ambulatory Monitoring of Posture Change Using Miniature Electro–Magnetic Inclinometers" Medical & Biological Engineering & Computing 32(3), May 1994, pp. 357–360.

* cited by examiner

Primary Examiner—Robert L. Nasser
Assistant Examiner—Navin Natnithithadha
(74) Attorney, Agent, or Firm—Morrison & Foerster LLP

(57) ABSTRACT

Blood pressure measurement is precisely performed by more correctly determining positions of a cuff and a heart without being affected by variations in physical features among subject persons and their postures during the measurement. With the technique of the present invention, there are calculated the altitudes of the cuff and the heart on the basis of an inputted upper arm length and forearm length of a subject person and forearm angles detected in the pitch direction and roll direction. Also, in addition to a forearm angle detecting means, an upper arm angle detecting means is provided and the altitudes of the cuff and the heart are calculated on the basis of detected angles of a forearm and an upper arm. Also, a biaxial angle detecting means detects angles of the forearm in the pitch direction and the roll direction and calculates the altitudes of the cuff and the heart on the basis of these detected values.

20 Claims, 36 Drawing Sheets

(A)

(B)

(A)

(B)

$X = L * \sin\theta * \cos\phi$
$Y = L * \cos\theta$
$Z = L * \sin\theta * \sin\phi$

ELECTRONIC SPHYGMOMANOMETER

TECHNICAL FIELD

The present invention relates to an electronic sphygmomanometer having a function of detecting the posture of a subject person.

BACKGROUND ART

It is possible for a general sphygmomanometer to obtain a precise blood pressure value when blood pressure measurement is performed under a condition where a cuff is raised and the altitude thereof becomes the same as the altitude of a heart. However, in the case of an electronic sphygmomanometer applied to a wrist, an electronic sphygmomanometer applied to a finger, or the like, the sphygmomanometer is used under a condition where a cuff (integrated with a main body in many cases) is placed on the wrist, finger, or another predetermined region. The wrist and finger are regions that are capable of freely moving, so that it is impossible to set these parts so that the altitudes thereof become the same as the altitude of a heart. Therefore, there may be cases where it becomes impossible to precisely measure blood pressures.

To avoid such a problem, with a conventional technique, a uniaxial angle detecting apparatus is provided for a cuff or in the vicinity thereof, the positional relation between the cuff and a heart is determined from an angle detected by the apparatus, and there is notified a result of the determination.

However, if the positional relation between the heart and the cuff is determined only from uniaxial angle information like in the case of the conventional technique described above, various error causing factors affect the accuracy of the blood pressure measurement.

As such error causing factors, there may be first cited variations in upper arm length and forearm length among subject persons. For instance, FIG. 32 shows a case where measurement is performed for different forearm lengths L1 and L1a. Even if the same inclination angle of a forearm is maintained, there occurs a difference in altitude between a cuff 100 and a heart 101. That is, in the case where the forearm length is L1, the altitude of the cuff 100 becomes the same as the altitude of the heart 101. However, in the case where the forearm length is L1a, the actual position of a cuff 100a becomes lower than the position of the heart 101 by ΔH. Accordingly, if it is determined that this detected inclination angle is correct, there may be a case where it becomes impossible to precisely measure a blood pressure due to the variation in forearm length. As shown in FIG. 33, in case where the forearm length L1 and the inclination angle are not changed and the upper arm lengths L2 and L2a are different, for the upper arm length L2, the altitude of the cuff 100 becomes the same as the altitude of the heart 101, on the other hand, for the upper arm length L2a, the position of the cuff 100a becomes higher than the position of the heart 101 by ΔH. Accordingly, if it is determined that this inclination angle is correct, there may be a case where it becomes impossible to precisely measure a blood pressure due to the variation in upper arm length.

Also, even if the same angle of a forearm is maintained, there may be a case where the altitude of a heart differs from the altitude of the center of a cuff depending on the angle of an upper arm of a subject person, which is to say the position of his/her elbow, which causes an error. FIGS. 34 and 35 show examples of such a case. In FIG. 34A, the altitude of the cuff 100 is the same as the altitude of the heart H and the difference ΔH becomes zero under a condition where an upper arm L2 extends vertically. Even if the detected angle of a forearm is the same as that in FIG. 34A, under a condition where the upper arm L2 is tilted in the left-and-right direction (pitch direction) in front of a body as shown in FIG. 34B, the center of the cuff 100 is positioned higher than the heart H by ΔH. In a like manner, under a condition where the upper arm L2 is tilted in a back-and-forth direction (roll direction) of the body as shown in FIG. 35, the center of the cuff 100 is also positioned higher than the heart H by ΔH. Accordingly, if it is determined that the altitude of the cuff is the same as the altitude of the heart in the cases shown in FIGS. 34B and 35 because the inclination angle of the forearm L1 is the same as that shown in FIG. 34A, there occurs a problem in that erroneous results are obtained.

Also, in the case where a space is generated between an elbow and a body due to the movement of an upper arm and in the case where the body is inclined, even if the same angle of a forearm is maintained in the pitch direction, there may occur a difference between the altitudes of the heart H and the center of the cuff 100. There may be the cases where this causes an error. For example, in FIG. 36 there are shown a case where the body is inclined by 0° as indicated by a dotted line and a case where the body is inclined by 30° as indicated by a solid line. If the body is tilted while maintaining the same posture, the angle of the forearm with respect to a horizontal plane becomes small, so that the position of a sphygmomanometer is displaced from the position of the heart when the subject person tries to position the sphygmomanometer within a predetermined range. Also, as indicated by the solid line in FIG. 37, if the forearm is tilted with respect to a vertical direction, the position of the sphygmomanometer is displaced from the position of the heart like in the case shown in FIG. 36.

The present invention has been made to solve these problems of the conventional technique, and is aimed at providing an electronic sphygmomanometer that is capable of precisely measuring a blood pressure by more precisely determining the positions of a cuff and a heart.

BRIEF SUMMARY OF THE INVENTION

An electronic sphygmomanometer of the present invention comprises: measuring means that is placed on a predetermined region and measures one of a blood pressure and hemodynamics; posture detecting means for detecting a posture of a subject person; propriety determining means for determining whether the measurement using the detected posture; and a notifying means for notifying a result of the determination by the propriety determining means, wherein the posture detecting means includes: a living body information inputting unit to input living body information of the subject person; and an altitude detecting unit for detecting an altitude of a measurement region based on the living body information.

With this electronic sphygmomanometer, the posture of the subject person is detected using the altitude of the measurement region and the inputted living body information of the subject person. As a result, it becomes possible to determine whether measurement is proper or not without being affected by physical variations among subject persons.

Also, another electronic sphygmomanometer of the present invention comprises: measuring means that is placed on a predetermined region and measures one of a blood pressure and hemodynamics; posture detecting means for detecting a posture of a subject person; blood pressure value correcting means for correcting a blood pressure value measured by the blood pressure measuring means in accordance with the detected posture; and display means for displaying the corrected blood pressure value, wherein the posture detecting means includes: altitude detecting means for detecting an altitude of a measurement region; and living body information inputting means for inputting living body information of the subject person.

With this electronic sphygmomanometer, the posture of the subject person is detected using an angle of the measurement region and the inputted living body information of the subject person, and the measured blood pressure value is corrected using this detected posture. As a result, it becomes possible to precisely measure a blood pressure without being affected by physical variations among subject persons.

A still another electronic sphygmomanometer of the present invention comprises: measuring means that is placed on a predetermined region and measures one of a blood pressure and hemodynamics; posture detecting means for detecting a posture of a subject person; propriety determining means for determining whether the measurement using the detected posture is proper or not; notifying means for notifying a result of the determination by the propriety determining means; and upper arm angle measuring means that is separated from a main body and detects an angle of an upper arm.

With this electronic sphygmomanometer, the upper arm angle measuring means that is separated from the main body detects the angle of the upper arm. Therefore, the angle of an arm as well as the angle of a forearm are reflected in the calculation of the positional relation between a cuff and a heart with regard to the altitudes thereof. As a result, it becomes possible to determine whether measurement is proper or not without being affected by the inclination of the upper arm.

Also, another electronic sphygmomanometer of the present invention comprises: measuring means that is placed on a predetermined region and measures one of a blood pressure and hemodynamics; posture detecting means for detecting a posture of a subject person; blood pressure value correcting means for calculating a blood pressure value corrected in accordance with the detected posture as a blood pressure value measured by the measuring means; display means for displaying the corrected blood pressure value; and upper arm angle detecting means that is separated from a main body and detects an angle of an upper arm.

With this electronic sphygmomanometer, the upper arm angle detecting means that is separated from the main body detects the angle of the upper arm and the angle of the upper arm as well as the angle of a forearm are reflected in the calculation of the positional relation between a cuff and a heart with regard to the altitudes thereof. Then, a blood pressure value is precisely corrected. As a result, it becomes possible to precisely measure a blood pressure without being affected by inclination of the upper arm.

Another electronic sphygmomanometer of the present invention comprises: measuring means that is placed on a predetermined region and measures one of a blood pressure and hemodynamics; biaxial angle detecting means for detecting angles of two axes; measurement posture altitude difference calculating means for calculating an altitude difference in a vertical direction between a heart of a subject person and a predetermined reference position of the sphygmomanometer using the angle detected by the biaxial angle detecting means; measurement posture propriety determining means for determining whether the calculated altitude difference exists within a predetermined altitude difference range using a result of the calculation by the measurement posture altitude difference calculating means; and notifying means for notifying the subject person of a result of the determination by the measurement posture propriety determining means. By detecting the angles of two axes in this manner, it becomes possible to more precisely calculate the altitude difference in the vertical direction between the heart of the subject person and the predetermined reference position of the sphygmomanometer. As a result, it becomes possible to more exactly determine a measurement posture.

Also, another electronic sphygmomanometer of the present invention comprises: measuring means that is placed on a predetermined region and measures one of a blood pressure and hemodynamics; biaxial angle detecting means for detecting angles of two axes; measurement posture altitude difference calculating means for calculating an altitude difference in a vertical direction between a heart of a subject person and a predetermined reference position of the sphygmomanometer using the angle detected by the biaxial angle detecting means; correction pressure calculating means for calculating a correction value for a blood pressure using a result of the calculation by the measurement posture altitude difference calculating means; post-correction blood pressure calculating means for calculating a post-correction blood pressure value using the correction value calculated by the correction pressure calculating means and a blood pressure value measured by the measuring means; and measurement result notifying means for notifying the subject person of a result of the calculation by the post-correction blood pressure calculating means. By detecting the angles of two axes in this manner, it becomes possible to precisely calculate the altitude difference in the vertical direction between the heart of the subject person and the predetermined reference position of the sphygmomanometer. A blood pressure value is corrected on the basis of a value obtained as a result of this calculation, so that it becomes possible to more precisely measure a blood pressure.

DETAILED DESCRIPTION OF THE INVENTION (First Embodiment)

The present invention will be described in more detail below by means of embodiments.

Figure 1:
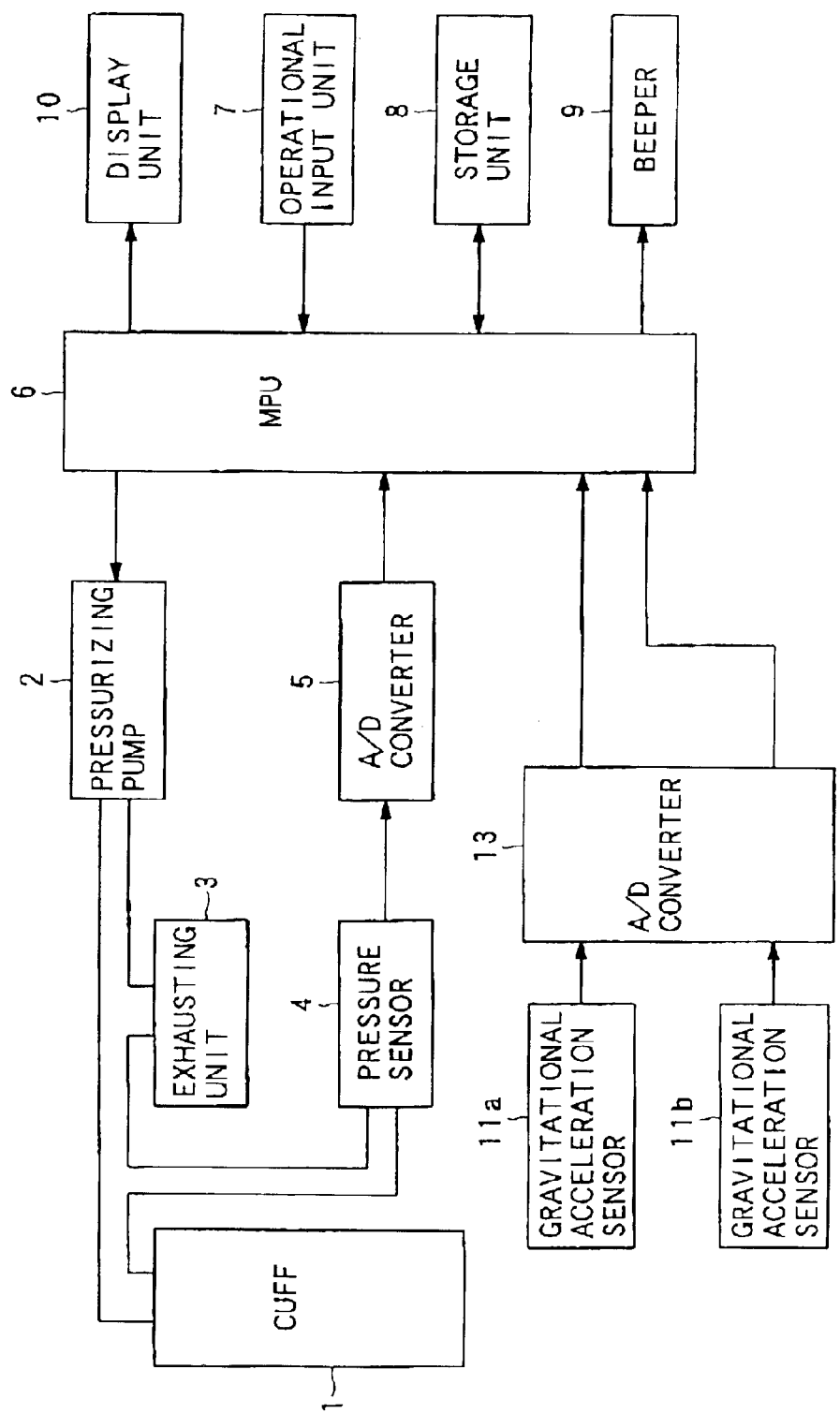
FIG. 1 is a block diagram showing the construction of an electronic sphygmomanometer according to the first embodiment of the present invention.

FIG. 1 is a block diagram showing the hardware construction of an electronic sphygmomanometer according to the first embodiment of the present invention. This electronic sphygmomanometer includes: a cuff 1; a pressurizing pump 2 for pressurizing this cuff 1; and exhausting unit 3 for exhausting air from the cuff1; a pressure sensor 4 for detecting an air pressure in the cuff 1; an A/D converter 5; an MPU 6 that performs processing for measuring a blood pressure by executing an installed program; an operational input unit 7 including a pressurizing key, keys for inputting a forearm length and an upper arm length, and other keys; a storage unit if the body is inclined while maintaining the same angle of a forearm in the pitch direction, the positional relation between the heart and the main body changes in the vertical direction. It is possible to reduce an altitude dejection error due to this phenomenon by measuring a reclining angle under a condition where there is maintained a measurement posture in which the arm is held along the body.

The electronic sphygmomanometer according to this embodiment has a construction where it is possible to input the forearm length and upper arm length of a subject person using the operational input unit 7. With this construction, it becomes possible to precisely detect the altitude of the apparatus from the inputted forearm length, the inputted upper arm length, and the posture angle detected by the angle detector 11.

Here, the principle adopted by the electronic sphygmomanometer according to this embodiment will be described.

Figure 2:
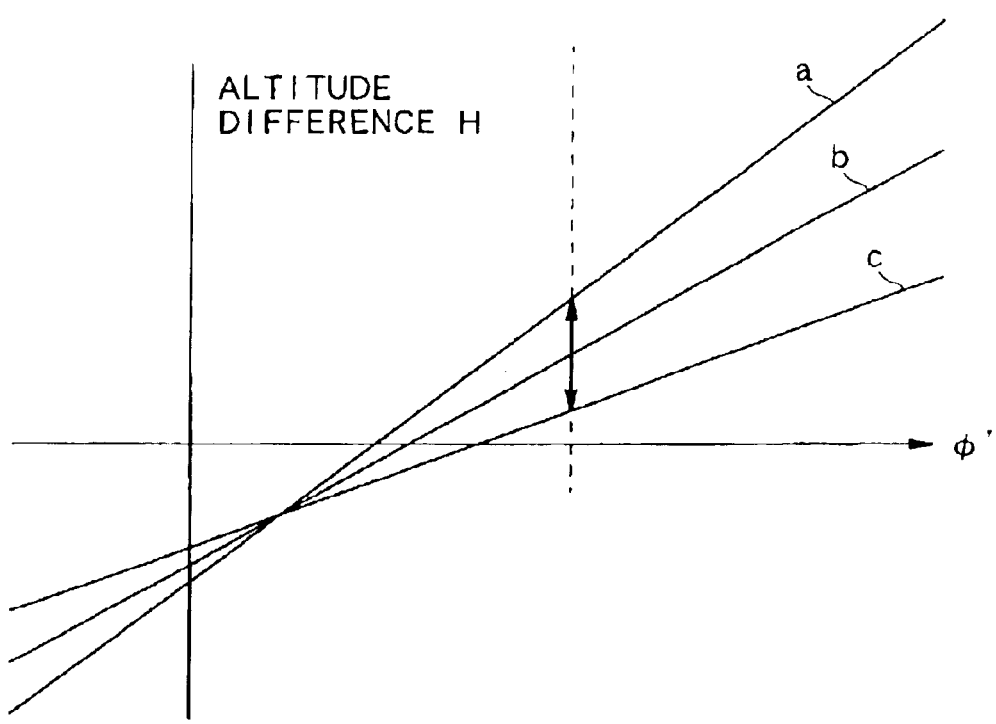
FIG. 2 is a characteristic diagram showing how a difference between the inclination angle of an arm and the altitude of the arm changes during the measurement of a blood pressure due to variations in forearm length and upper arm length.

With a conventional electronic sphygmomanometer, the inclination angle of the apparatus is detected and the altitude of the apparatus (cuff) is calculated from the detected inclination angle. However, if the altitude is detected only from the angle information in this manner, the altitude difference with the actual altitude of a heart greatly varies depending on the length of an arm even if the same angle is maintained as shown in FIG. 2. That is, the relation between an inclination angle φ' and an altitude difference H varies as follows: The relation becomes a correlation straight line "a" in the case where the forearm length and upper arm length of a subject person are long. The relation becomes a correlation straight line "b" in the case where the forearm length and upper arm length of the subject person are normal. The relation becomes a correlation straight line "c" in the case where the forearm length and upper arm length of the subject person are short.

Figure 3:
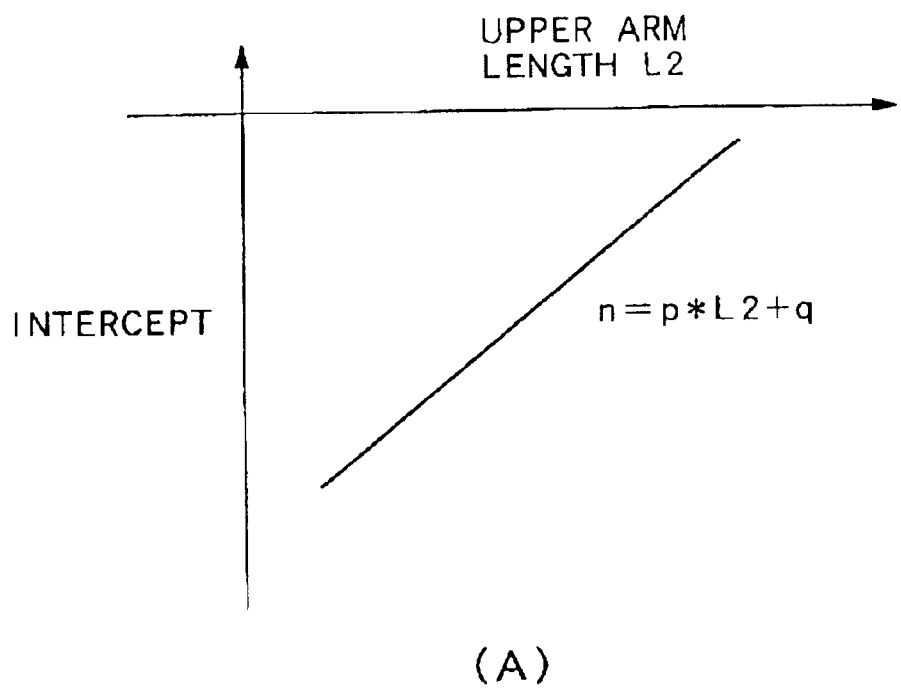
FIG. 3 respectively show a relation between an upper arm length and an intercept and a relation between a forearm length and inclination in the case of the characteristic diagram shown in FIG. 2.
Figure 3:
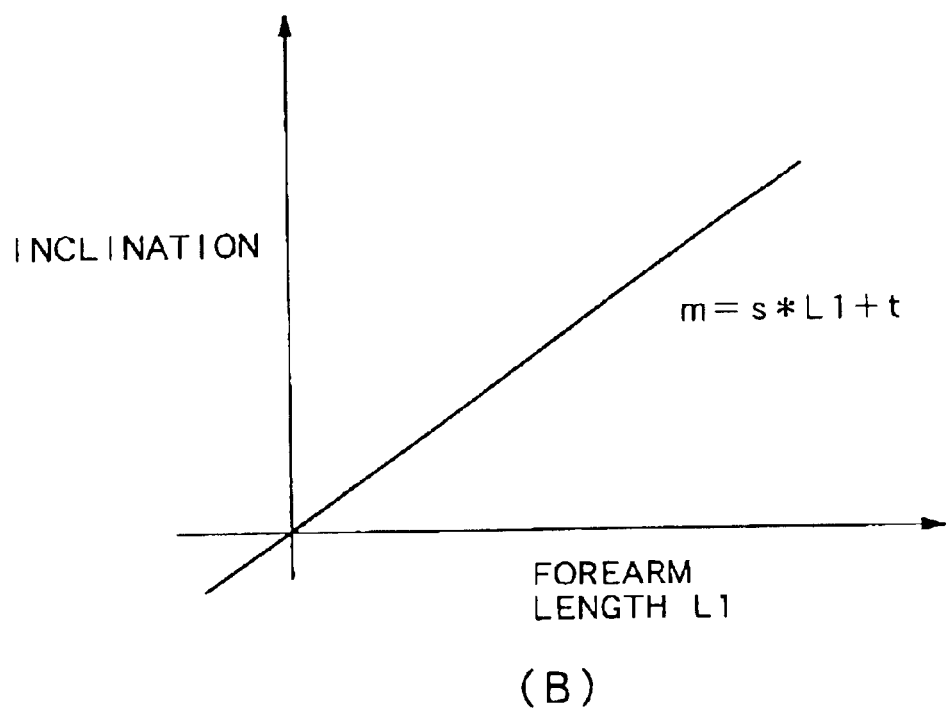

With the electronic sphygmomanometer of this embodiment, the forearm length and the upper arm length are inputted, so that it becomes possible to predict the Y intercept and gradient of each correlation straight line shown in FIG. 2 from the upper arm length L2 and the forearm length L1. The result of a relation between the upper arm length L2 and the intercept is shown in FIG. 3A and the result of a relation between the forearm length L1 and inclination is shown in FIG. 3B.

Figure 4:
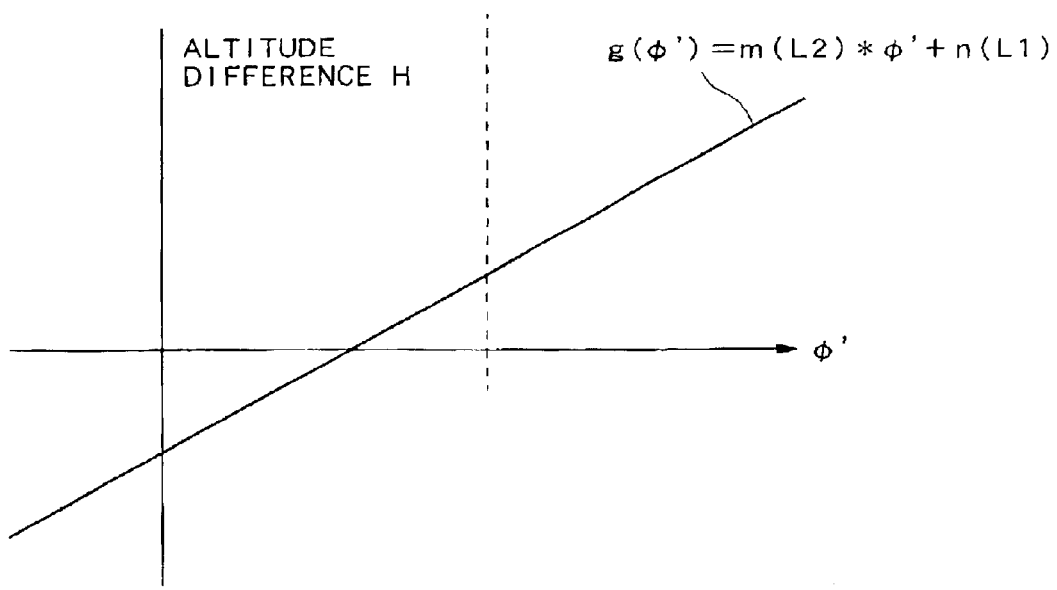
FIG. 4 shows a relation between an inclination angle and an altitude difference where an upper arm length and a forearm length are taken into account.

From these results, a difference ΔH becomes ΔH=f(φ')= g(φ', L1, L2) and it becomes possible to eliminate variations in upper arm length and forearm length. This avoids a situation where the accuracy of the altitude detection is affected by the variations in upper arm length and forearm length among subject persons. That is, as shown in FIG. 4, the altitude difference H with respect to a detection angle φ' becomes g(φ')=m(L1)*φ'+n(L2). Therefore, it is possible to detect the correct altitude of the apparatus (cuff) from this equation by taking into consideration the upper arm length L1 and the forearm length L2.

Figure 5:
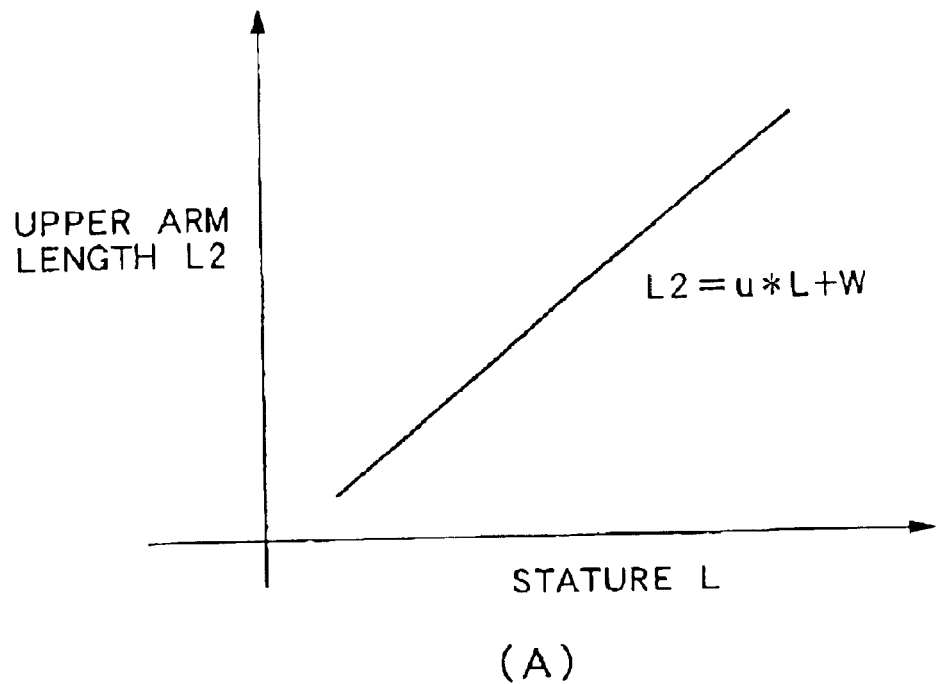
FIG. 5 respectively show a relation between a stature L and an upper arm length and a relation between the stature L and a forearm length.
Figure 5:
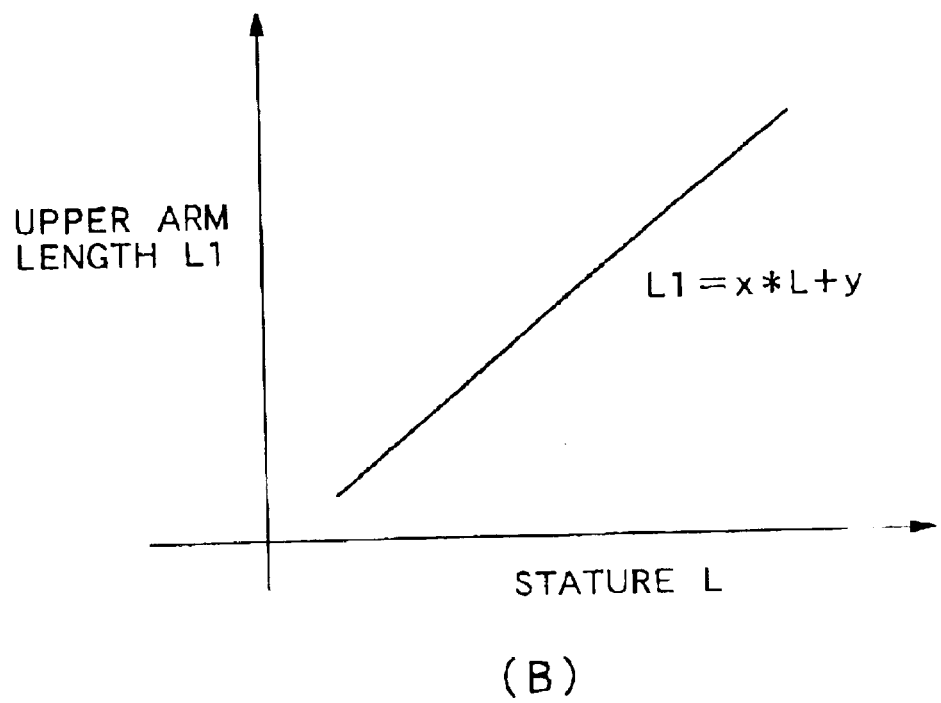

Also, as shown in FIGS. 5A and 5B, there exists a correlation between the upper arm length L2 and the stature L and there also exists a correlation between the forearm length L1 and the stature L. Therefore, by setting H=g(Φ', L1, L2) as H=h(Φ', L), it becomes possible to eliminate errors about the altitude detection due to the variations in upper arm length and forearm length merely by inputting the stature.

The aforementioned electronic sphygmomanometer includes the stated function of detecting the altitude of the cuff from the inclination angle, upper arm length, and forearm length mentioned above.

Figure 6:
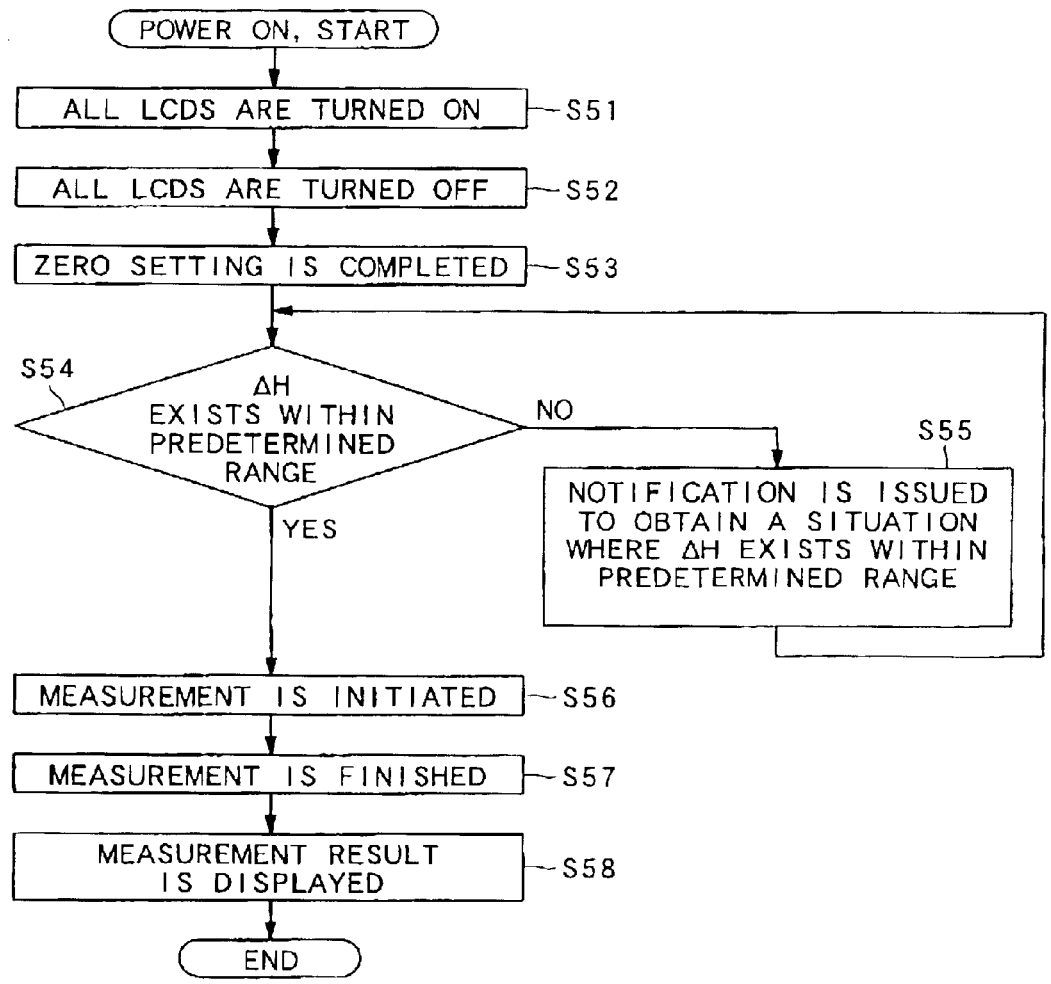
FIG. 6 is a flowchart illustrating a measurement processing operation of the electronic sphygmomanometer according to the first embodiment.

Next, the processing operation of this electronic sphygmomanometer will be described with reference to the flowchart shown in FIG. 6. When power is turned on and the operation is started, all of LCDs (display devices) are first turned on (step ST1). Following this, all of the LCDs are turned off (step ST2) to obtain a situation where it is possible to confirm the display function. Then, zero setting, which is to say initial reset, is completed (step ST3). Next, the display unit 10 performs a display operation to request the input of an upper arm length and a forearm length, and the input of the upper arm length and forearm length of the subject person is received (step ST4). An altitude difference is obtained from the posture angle detected by the angle detecting unit 11 and the inputted upper arm length and forearm length of the subject person and it is determined whether a forearm angle, which shows whether the apparatus exists within a predetermined range, exists within a predetermined range (step ST5). If the forearm angle does not exist within the predetermined range, a notification showing this situation is issued, that is, a message "Please raise the apparatus to some extent" or "Please lower the apparatus to some extent" is displayed, the beeper is turned on for notification(step ST9). Then, the processing returns to step ST5.

If the forearm angle enters into the predetermined range as a result of an altitude correction or exists within the predetermined range from the beginning, the pressurizing pump is turned on and measurement is initiated (step ST6). When the measurement of the highest blood pressure, the lowest blood pressure, and the pulse rate is finished (step ST7), measurement results are displayed (step ST8) and the operation is ended.

(Second Embodiment)

Figure 7:
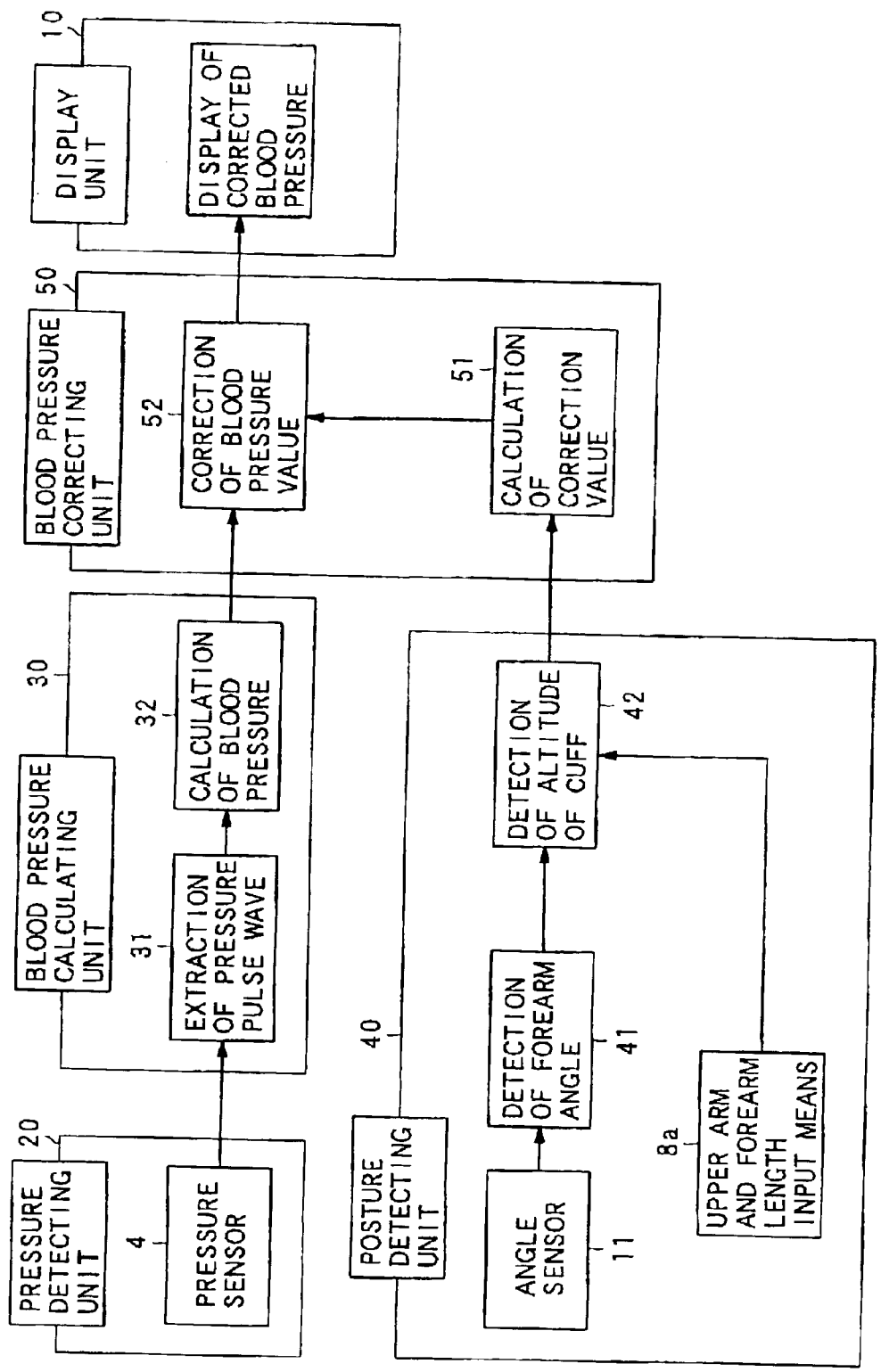
FIG. 7 is a block diagram showing the functional construction of an electronic sphygmomanometer according to the second embodiment of the present invention.

FIG. 7 is a block diagram showing the functional construction of an electronic sphygmomanometer according to the second embodiment of the present invention. The electronic sphygmomanometer according to this embodiment includes; a pressure detecting unit 20 including a pressure sensor 4; a pressure pulse wave detecting unit 31; a blood pressure calculating unit 30 including a blood pressure value calculating unit 32; an upper arm and forearm length inputting means 8a; an angle sensor 11; a forearm angle detecting unit 41; a posture detecting unit 40 including a cuff altitude detecting unit 42; a correction value calculating unit 51; a blood pressure correcting unit 50 including a blood pressure value correcting unit 52; and a display unit 10. The hardware construction of the electronic sphygmomanometer according to this embodiment is the same as that shown in FIG. 1. The function of each of the pressure pulse wave detecting unit 31, the blood pressure value calculating unit 32, the cuff altitude detecting unit 42, the correction value calculating unit 51, the blood pressure value correcting unit 52, and the like is realized by software processing of the MPU 6 shown in FIG. 1.

Figure 8:
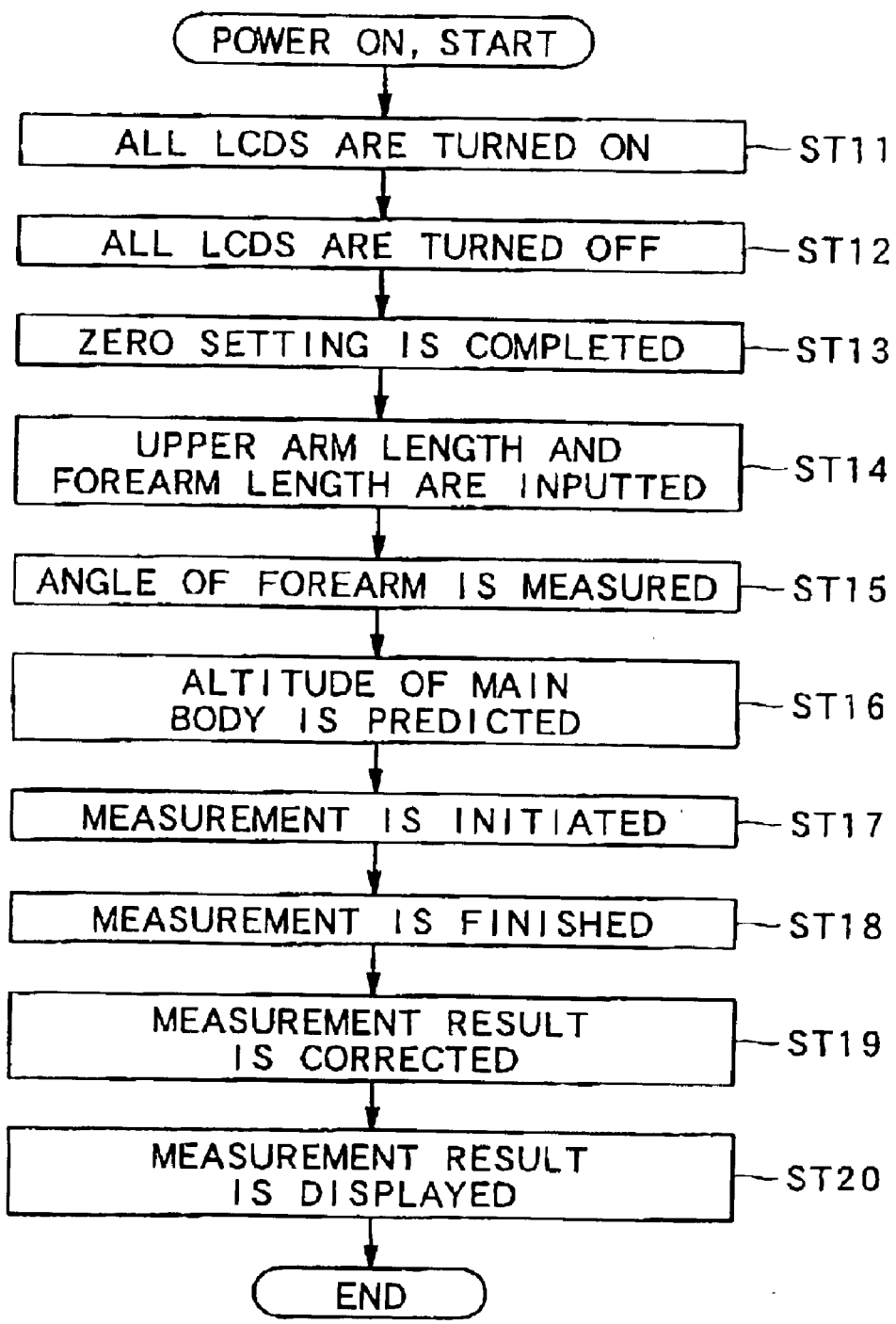
FIG. 8 is a flowchart illustrating a measurement processing operation of the electronic sphygmomanometer according to the embodiment.

Next, the processing operation of the electronic sphygmomanometer according to this embodiment will be described with reference to the flowchart shown in FIG. 8. When power is turned on and the operation is started, all of LCDs (display devices) are first turned on (step ST1). Following this, all of the LCDs are turned off (step ST12) and zero setting, which is to say initial reset, is completed (step ST13). Next, the display unit performs a display operation to request the input of an upper arm length and a forearm length, and the input of the upper arm length and the forearm length of a subject person is received by the upper arm and forearm length inputting unit 8a (step ST14).

Figure 9:
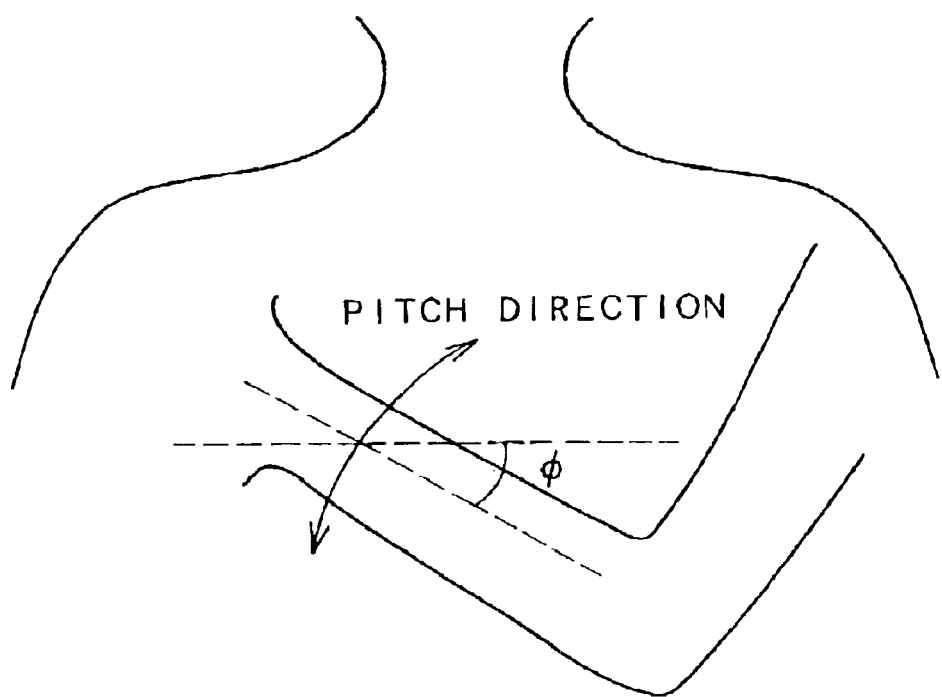
FIG. 9 illustrates an inclination angle in the pitch direction detected by an angle detector of the electronic sphygmomanometer according to the embodiment.
Figure 10:
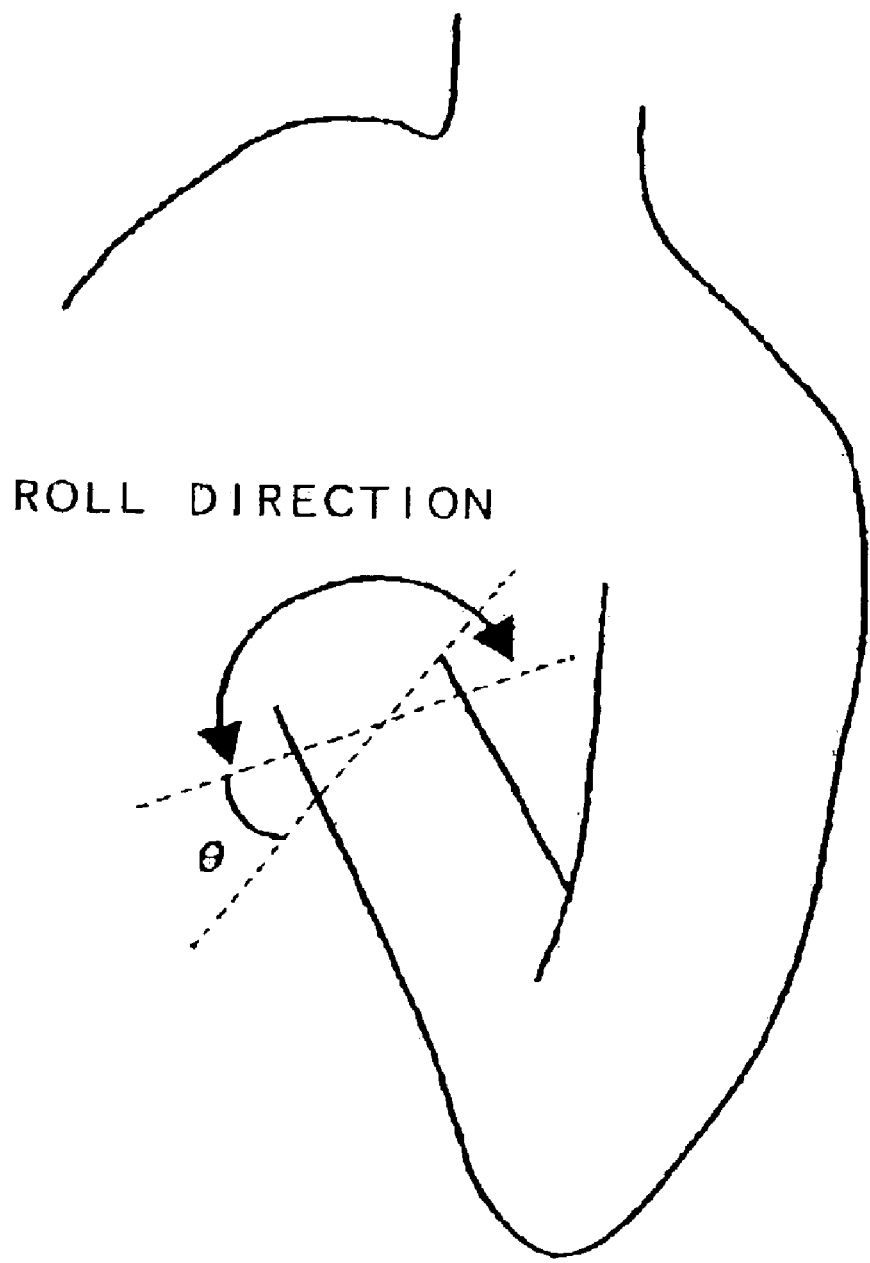
FIG. 10 illustrates an inclination angle in the roll direction detected by the angle detector of the electronic sphygmomanometer according to the embodiment.

Also, the angle of the forearm is measured by the angle sensor 11 and the forearm angle detecting unit 41 (step ST15). Here, the detected angle of the forearm is an angle φ in the pitch direction shown in FIG. 9 and an angle θ in the roll direction shown in FIG. 10. Next, the altitude of the main body is predicted on the basis of the inputted upper arm length L1, the inputted forearm length L2, and the detected angles φ and θ of the forearm (step ST16).

Figure 11:
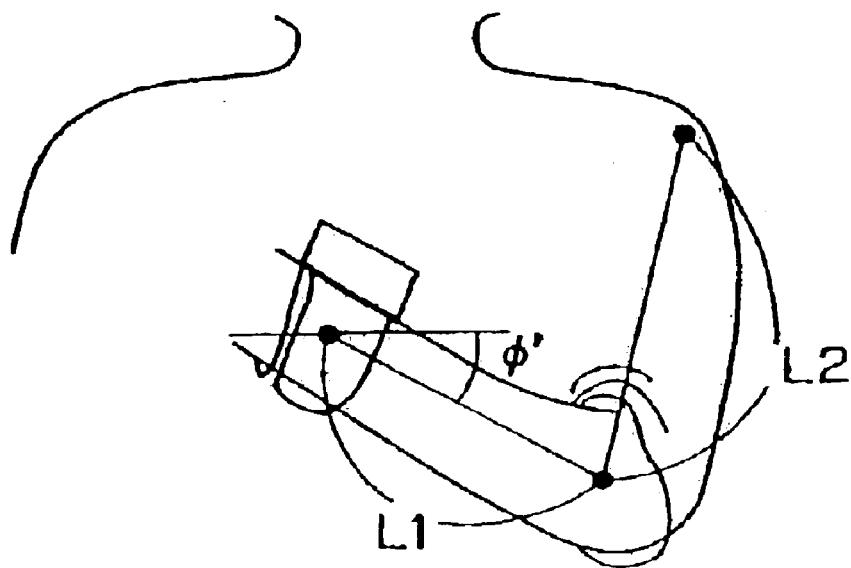
FIG. 11 illustrates how the electronic sphygmomanometer according to the embodiment calculates the altitude of a main body using the detected angle and the forearm length.
Figure 11:
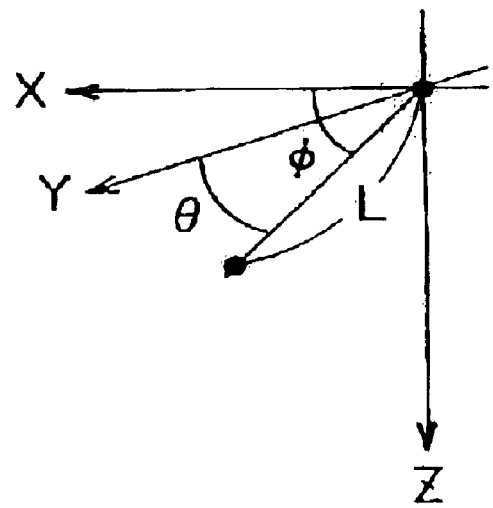

The prediction value of the altitude of the main body is calculated in the manner described below. Here, if a length is referred to as L, a pitch angle is referred to as φΦ, and a roll angle is referred to as φ, an altitude Z is generally obtained from an equation "Z=L*sin θ*sin φ". As a result, as shown in FIG. 11, if the forearm length is referred to as L1, it is possible to obtain the altitude of the main body from an elbow using an equation "H=L1*sin θ*sin φ". Following this, data showing this main body altitude is stored in a memory, the pressurizing pump is turned on, pressurizing is started, and measurement is initiated (step ST17). The measurement is performed by pressurizing a cuff to a pressurizing target value, terminating the pressurizing, detecting a pressure pulse wave in the cuff pressure using the pressure pulse wave detecting unit 31 during a depressurizing process. Alternatively, the measurement is performed by detecting a pressure pulse wave in the cuff pressure using the pressure pulse wave detecting unit during a pressurizing process and determining the highest blood pressure value and the lowest blood pressure value using the blood pressure calculating unit 32 with a publicly well known algorithm, for instance, with a vibration method from amplitude train data of each pulse wave. When the blood pressure measurement is finished (step ST18), the measurement (determination) result is next corrected (step ST19). During the blood pressure value correction, the correction value calculating unit 51 first obtains a value showing the difference in altitude between the heart and the cuff (main body), with the altitude of the cuff having been obtained by the cuff altitude detecting unit. Then, a pressure correction data corresponding to the difference value is given to the blood pressure value correcting unit 52, the determined blood pressure value is corrected, and the correction result is displayed on the display unit 10 as a measurement result (step ST20).

Figure 12:
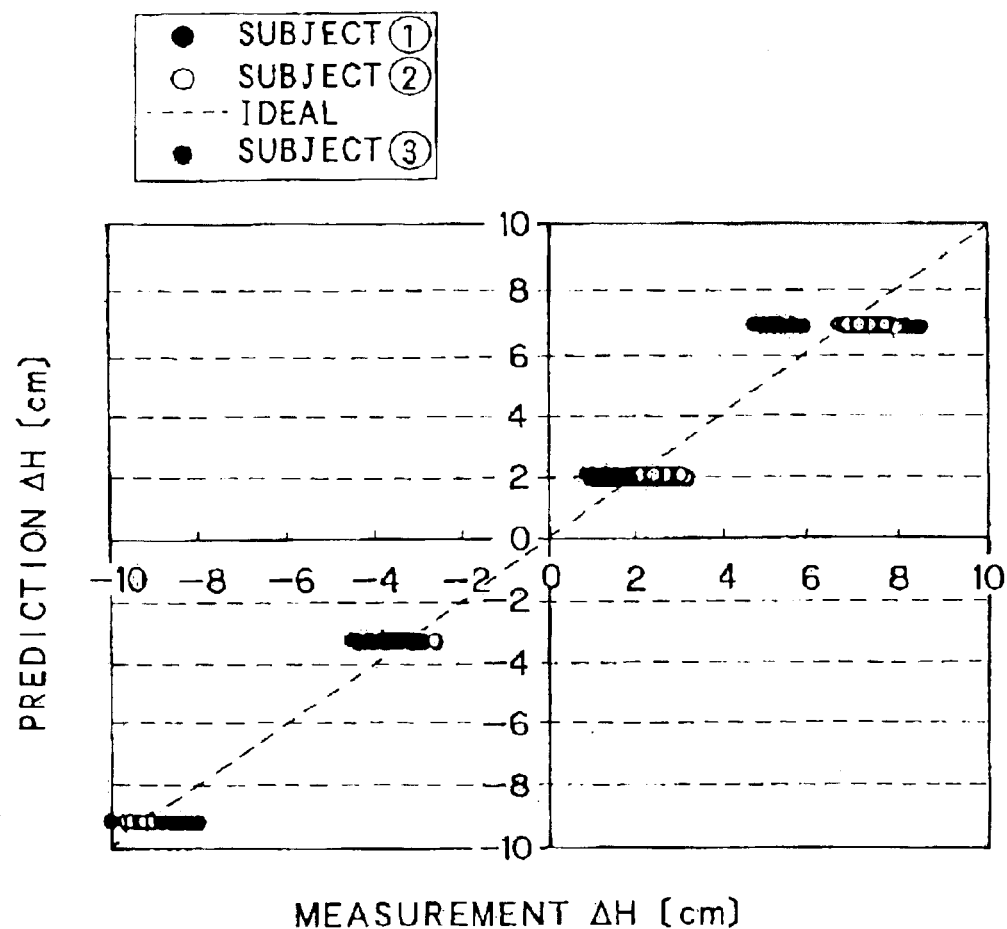
FIG. 12 is a characteristic diagram showing relations between measured altitudes and predicted altitudes of the main body obtained for subject person only through angle detection.
Figure 13:
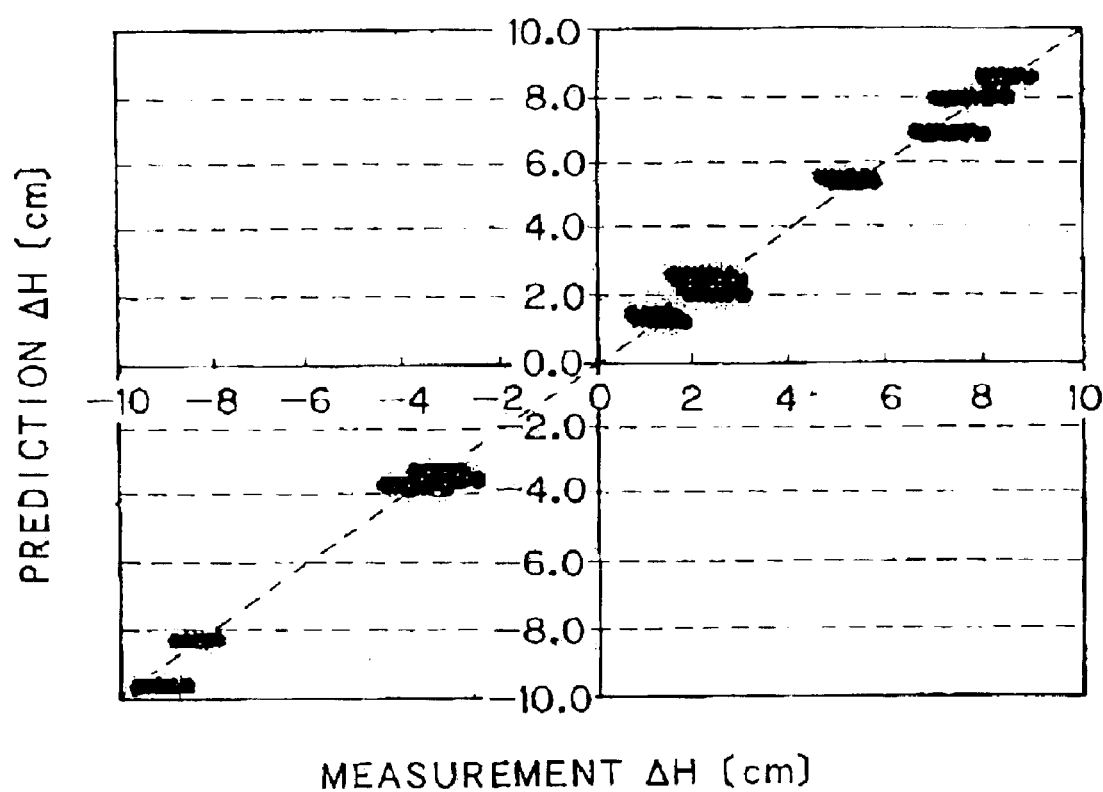
FIG. 13 is a characteristic diagram showing relations between measured altitudes and predicted altitudes of the main body obtained for subject person through angle detection and the inputs of upper arm lengths and forearm lengths.

As for the correction only using an angle and the correction using an angle, an upper arm length, and a forearm length, predicted ΔH (cm) and measured ΔH (cm) are obtained for three subject persons. It has been confirmed that less variations occur with the correction shown in FIG. 13 that uses an angle, an upper arm length, and a forearm length, in comparison with the case shown in FIG. 12 where correction was performed only using an angle. FIG. 12 shows an altitude detection characteristic (in the case of the correction only using an angle) obtained through theoretical analysis. In this case, the average value is 0.01 cm and the standard deviation is 1.08 cm. Also, FIG. 13 shows an altitude detection characteristic (in the case of the correction using an angle, an upper arm length, and a forearm length) obtained through theoretical analysis. In this case, the average value is −0.02 cm and the standard deviation is 0.41 cm.

Figure 14:
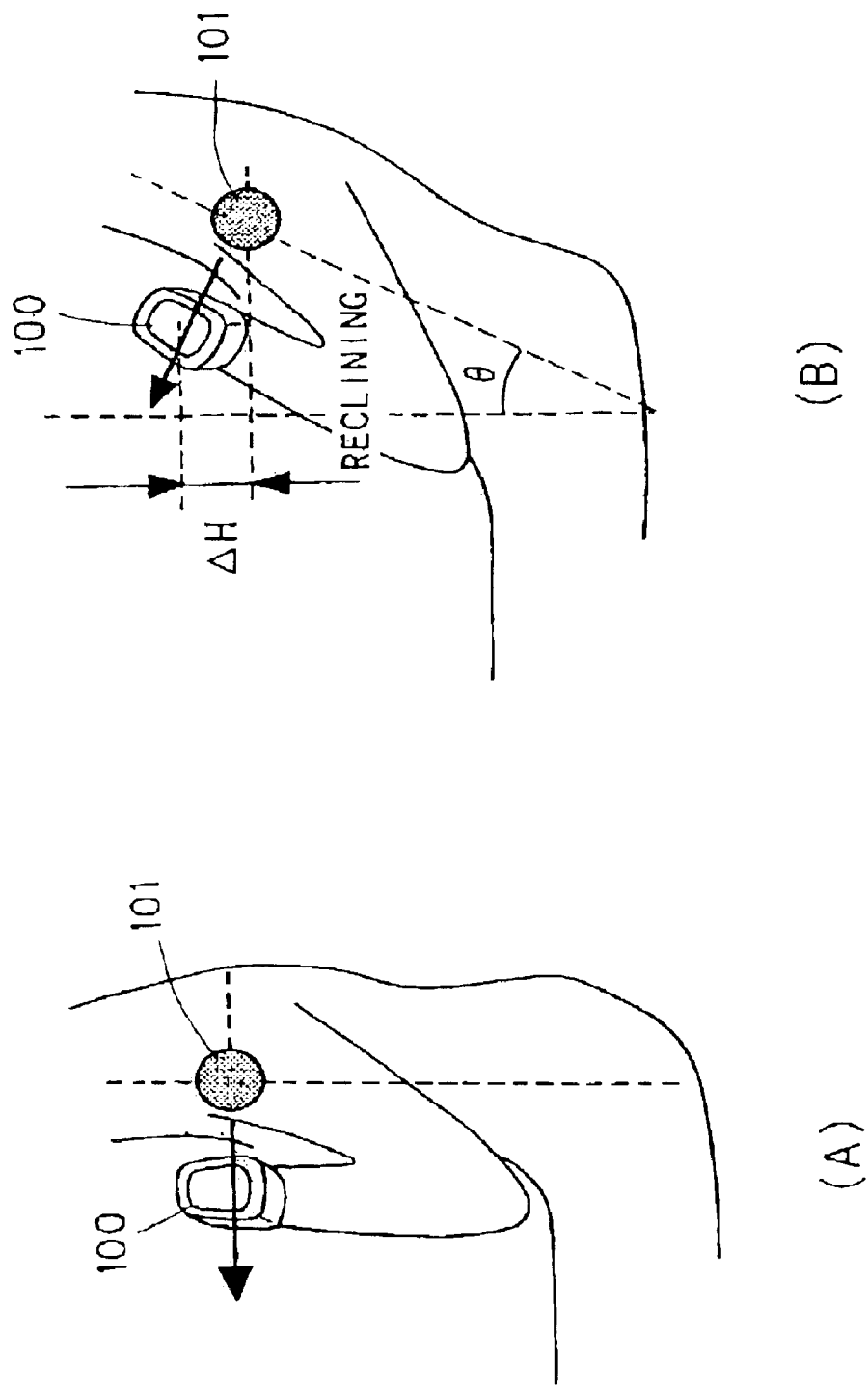
FIGS. 14A and 14B show a relation between the altitudes of the main body and a heart due to the inclination of the upper half of a body.

It should be noted here that with the electronic sphygmomanometer according to this embodiment, during the measurement of a blood pressure, as shown in FIGS. 14A and 14B, if the body is inclined while maintaining the same angle of a forearm in the pitch direction, the positional relation between the heart and the main body changes in the vertical direction. It is possible to reduce an altitude detection error due to this phenomenon by measuring a reclining angle under a condition where there is maintained a measurement posture in which the arm is held along the body.

(Third Embodiment)

Figure 15:
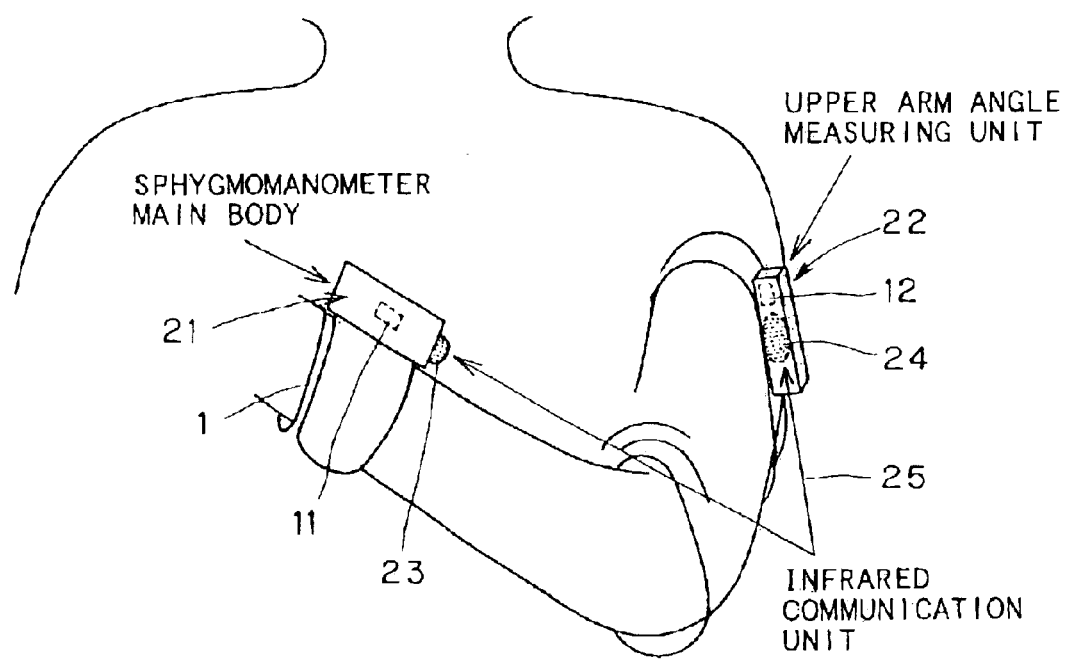
FIG. 15 shows a state where an electronic sphygmomanometer according to the third embodiment of the present invention is placed on an arm.

FIG. 15 shows a state where an electronic sphygmomanometer of the third embodiment of the present invention is placed. The electronic sphygmomanometer according to this embodiment includes a sphygmomanometer main body 21 and an upper arm angle measuring unit 22. The sphygmomanometer main body 21 and the upper arm angle measuring unit 22 include infrared transmission and reception devices 23 and 24, respectively, and perform data exchange by performing wireless communications using infrared rays 25.

Figure 16:
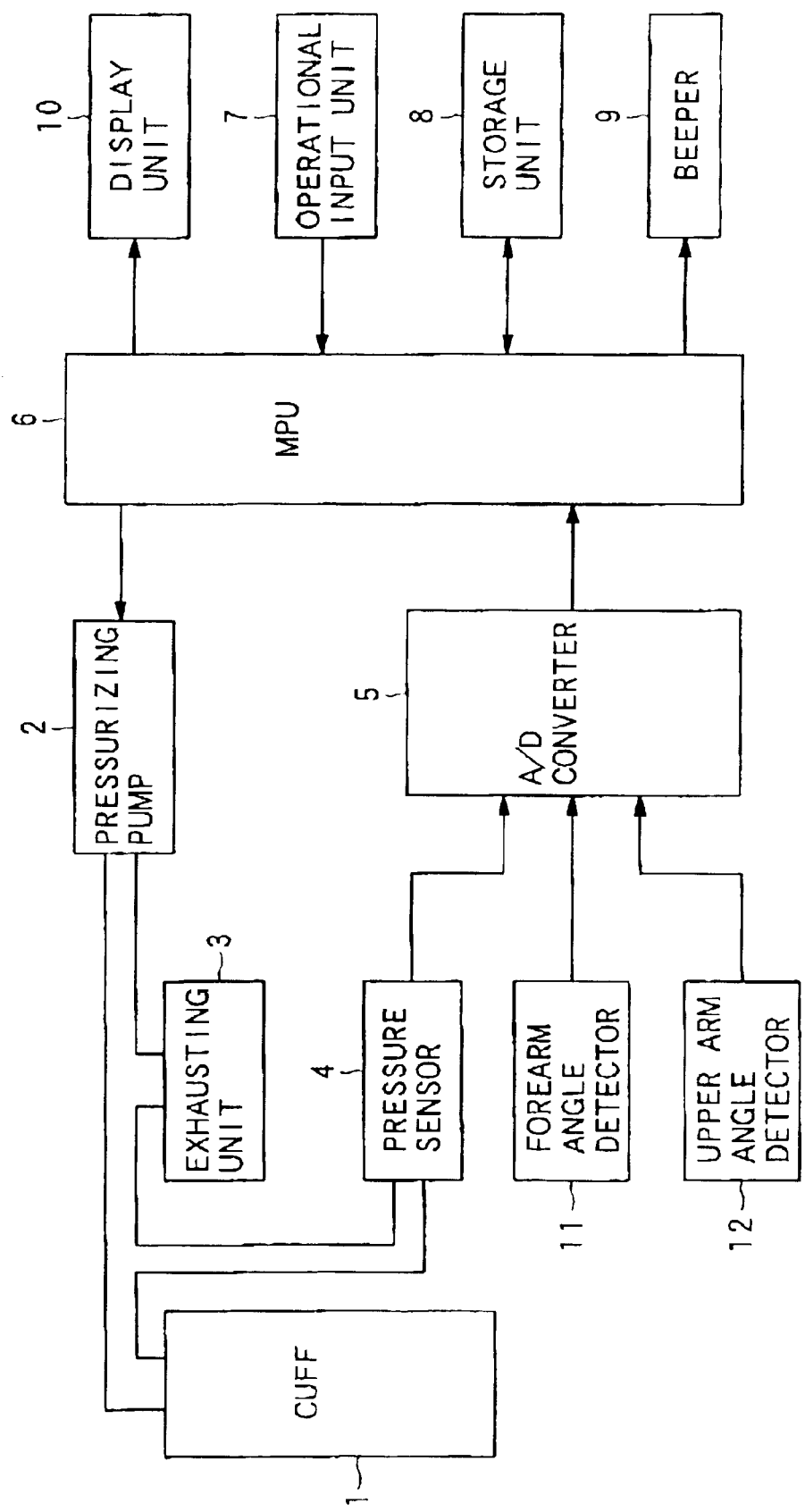
FIG. 16 is a block diagram showing the construction of an electronic sphygmomanometer according to the third embodiment of the present invention.

FIG. 16 is a block diagram showing the hardware construction of the electronic sphygmomanometer according to this embodiment. This electronic sphygmomanometer includes: a cuff 1; a pressurizing pump 2 for pressurizing this cuff 1; an exhausting unit 3 for exhausting air from the cuff 1; a pressure sensor 4 for detecting an air pressure in the cuff 1; an A/D converter 5; an MPU 6 that performs processing for measuring a blood pressure by executing an installed program; an operational input unit 7 including a pressurizing key and other keys; a storage unit 8 for storing input data, calculation data, a measurement result, and the like; a beeper 9 for issuing a notification; a display unit 10 for displaying a measurement result; a forearm angle detector 11 for detecting the posture angle of the main body of the sphygmomanometer (integrated with the cuff 1); and an upper arm angle detector 12 that is provided for a component separated from the main body.

Figure 17:
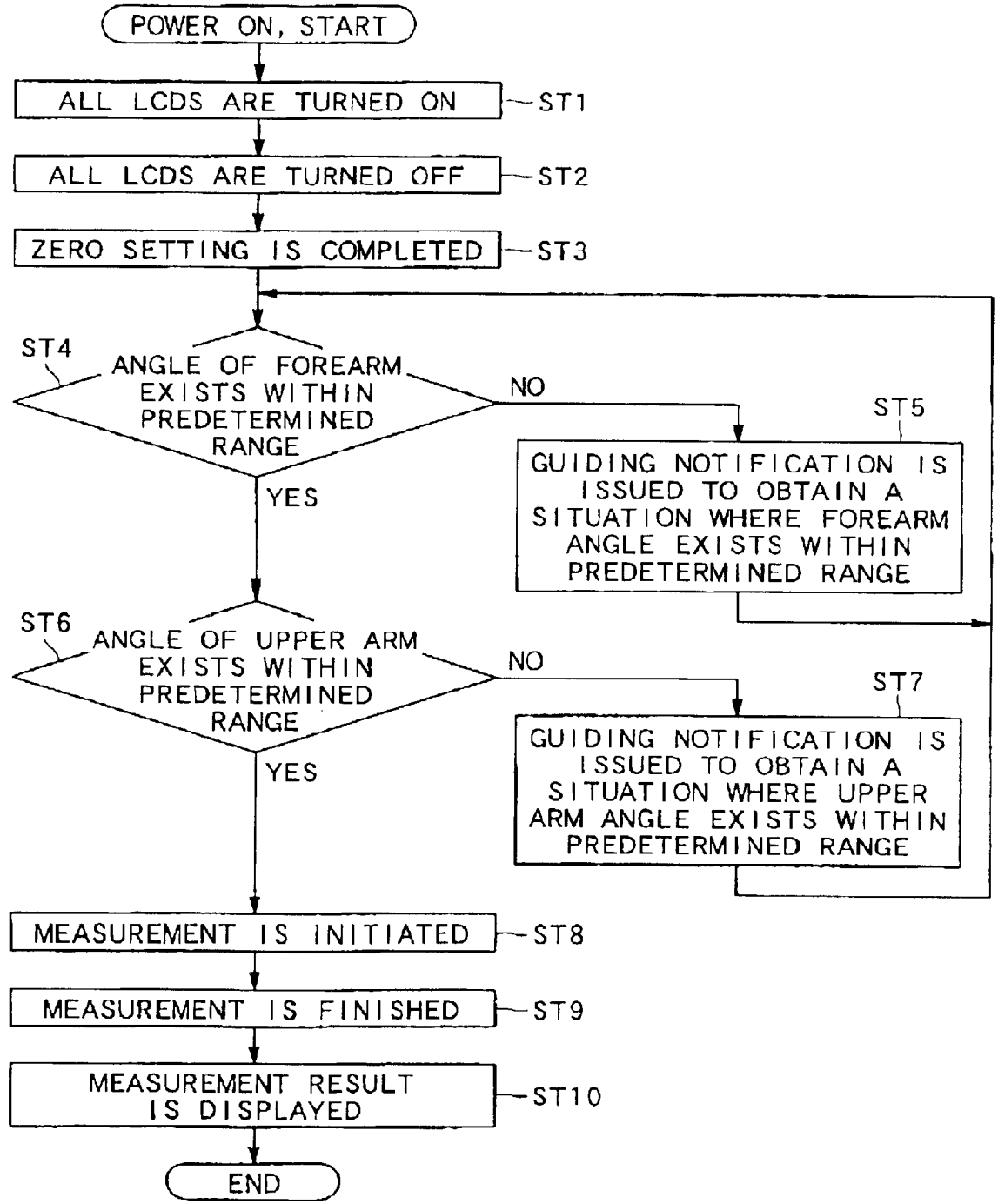
FIG. 17 is a flowchart illustrating a measurement processing operation of the electronic sphygmomanometer according to the above embodiment.

Next, the processing operation of the electronic sphygmomanometer according to this embodiment will be described with reference to the flowchart shown in FIG. 17. When power is turned on and the operation is started, all of LCDs (display devices) are first turned on (step ST31). Following this, all of the LCDs are turned off (step ST32) to obtain a situation where it is possible to confirm the display function. Then, zero setting, which is to say initial reset, is completed (step ST33). Next, it is determined whether an angle detected by the forearm angle detector 11 exists within a predetermined range (step ST34). If the angle of the forearm does not exist within the predetermined range, a guiding notification for obtaining an angle of the forearm existing within the predetermined range is issued. For instance, a message "Please raise the sphygmomanometer main body to some extent" is displayed (step ST35). If the forearm angle exists within the predetermined range or enters into the predetermined range, it is next determined whether an angle detected by the upper arm angle detector 12 exists within a predetermined range (step ST36). If the angle of the upper arm does not exist within a predetermined range, a guiding notification for obtaining an angle of the upper arm existing within the predetermined range is issued. For instance, a message "Please erect your upper arm to some extent" is displayed (step ST37). If the upper arm angle exists within the predetermined range or enters into the predetermined range, the pressurizing pump is turned on and measurement is initiated (step ST36). When the measurement of the highest blood pressure, the lowest blood pressure, and the pulse rate is finished (step ST37), measurement results are displayed (step ST38) and the operation is ended.

(Fourth Embodiment)

Figure 18:
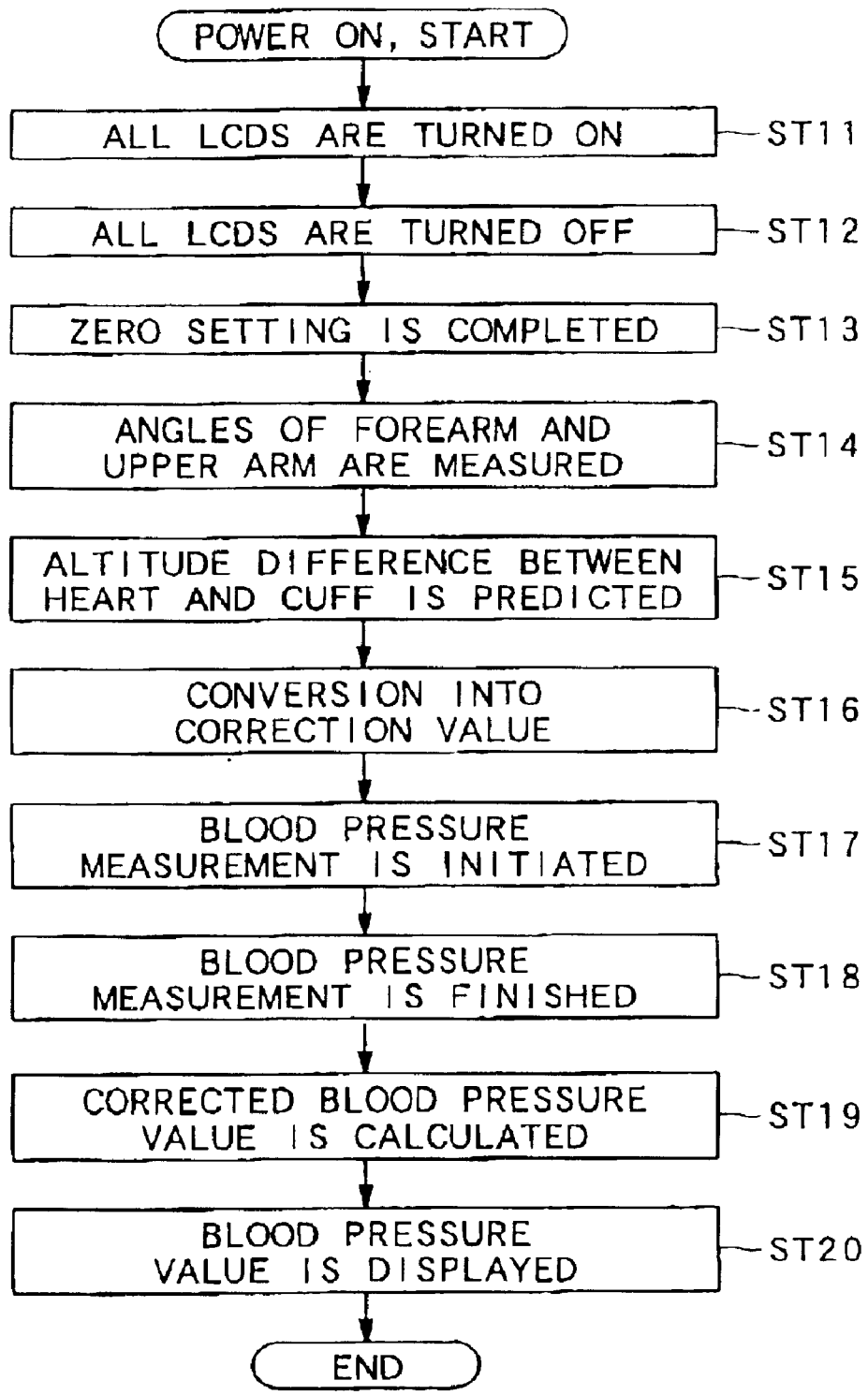
FIG. 18 is a flowchart illustrating a measurement processing operation of an electronic sphygmomanometer according to the fourth embodiment of the present invention.
Figure 19:
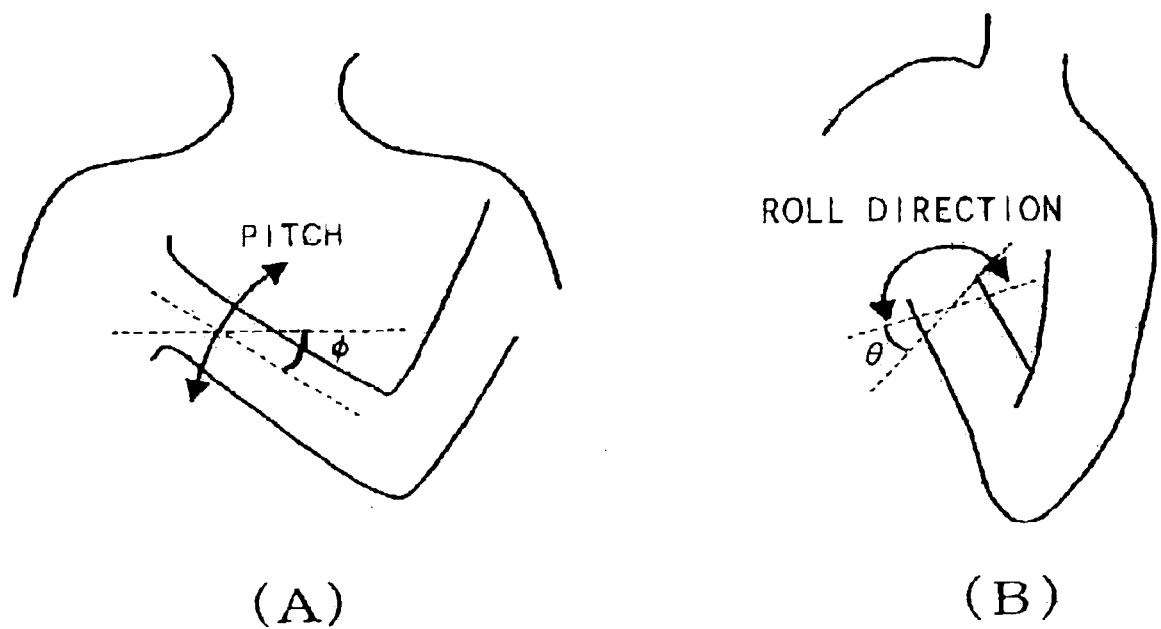
FIG. 19 respectively illustrate an inclination angle in the pitch direction and an inclination angle in the roll direction detected by an angle detector of the electronic sphygmomanometer according to the embodiment.
Figure 20:
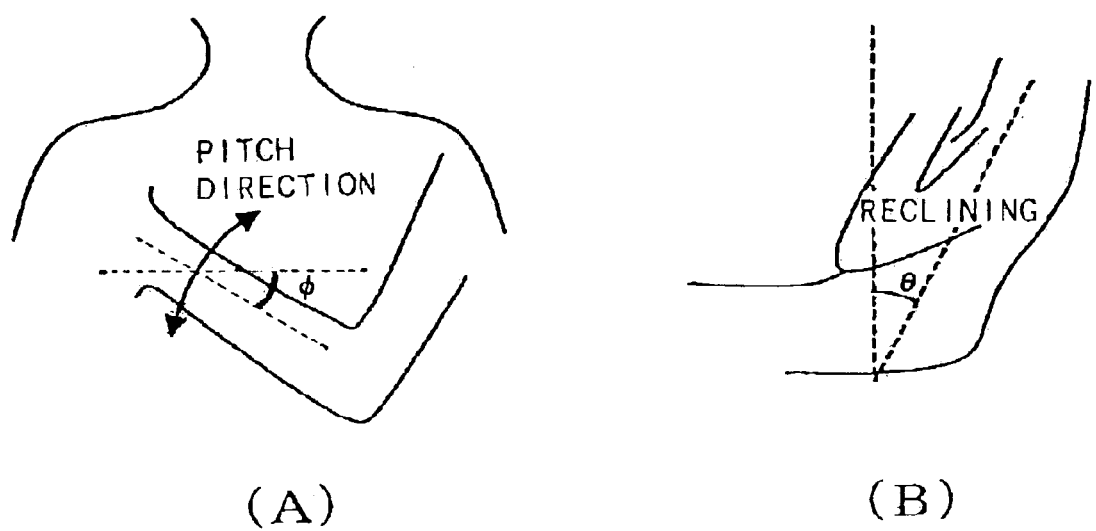
FIG. 20 respectively illustrate an inclination angle in the pitch direction and an inclination angle in a reclining direction detected by the angle detector of the electronic sphygmomanometer according to the embodiment.

FIG. 18 is a flowchart showing the processing operation of an electronic sphygmomanometer according to the fourth embodiment of the present invention. Note that the hardware construction of a circuit portion of the electronic sphygmomanometer according to this embodiment is the same as that shown in FIG. 16. As to the electronic sphygmomanometer according to this embodiment, when power is turned on and the operation is started, all of LCDs (display devices) are first turned on (step ST41) Following this, all of the LCDs are turned off (step ST42) and zero setting, which is to say initial reset, is completed (step ST43). Next, the angles of a forearm and an upper arm are detected by the forearm angle detector 11 and the upper arm angle detector 12 (step ST44). Here, the detected angle of the forearm is the angle Φ in the pitch direction shown in FIG. 19A and the angle φ in the roll direction shown in FIG. 19B. Alternatively, the detected forearm angle is the angle φ in the pitch direction shown in FIG. 20A and the angle θ in the reclining direction shown in FIG. 20B. Further, in some cases, the detected forearm angle is a combined angle of the angle θ in the pitch direction, the angle θ in the roll direction shown in FIG. 19B, and the angle θ in the reclining direction shown in FIG. 20B. The difference in altitude between the heart and the cuff is predicted from these detected forearm angle and upper arm angle (step ST45). Next, a value showing the predicted difference between the heart and the cuff is converted into a corresponding pressure correction value. This correction value is stored in a memory (step ST46). The pressurizing pump is turned on, pressurizing is started, and measurement is initiated (step ST47). The measurement is performed by pressurizing a cuff to a pressurizing target value, terminating the pressurizing, and detecting a pressure pulse wave in the cuff pressure during a depressurizing process. Alternatively, the measurement is performed by detecting a pressure pulse wave in the cuff pressure using the pressure pulse wave detecting unit during a pressurizing process and determining the highest blood pressure value and the lowest blood pressure value with a publicly well known algorithm, for instance, with a vibration method from amplitude train data of each pulse wave. When the blood pressure measurement is finished (step ST48), the measurement (determination) result is next corrected (step ST49). The blood pressure value correction is performed through calculation and correction to a blood pressure value determined on the basis of the pressure correction data stored in the memory. The corrected blood pressure value is displayed on the display unit 10 as a measurement result (step ST50).

With the electronic sphygmomanometer according to this embodiment, prior to the measurement of the angles of a forearm and an upper arm in step ST44, the forearm length and the upper arm length (living body information) of a subject person are inputted by the operational input unit 7. During the conversion into a correction value in step ST46, the correction may be performed by taking into account the variations in forearm length and upper arm length among subject persons. This correction about variations among subject persons using the forearm length and upper arm length inputted beforehand may be applied to the embodiment shown in FIG. 17.

Figure 21:
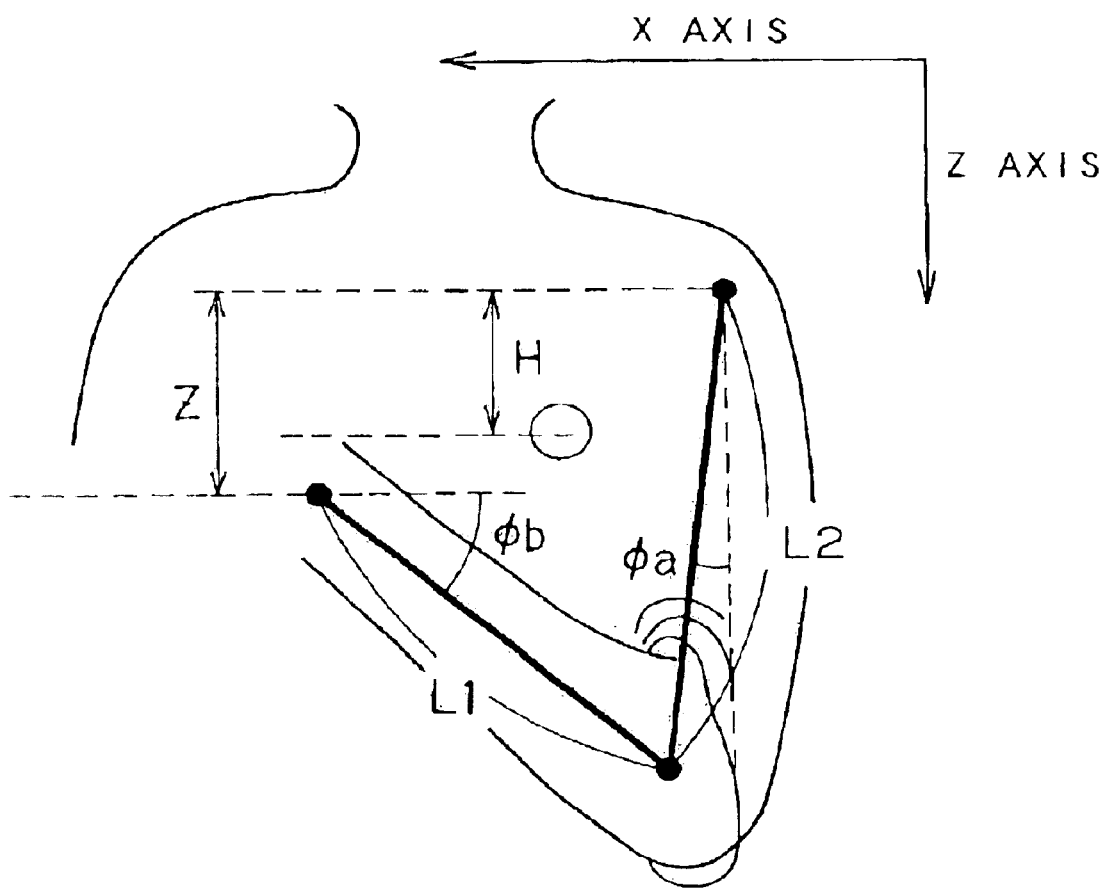
FIG. 21 illustrates how the electronic sphygmomanometer according to the embodiment calculates a difference ΔH between the altitudes of a cuff and a heart.
Figure 22:
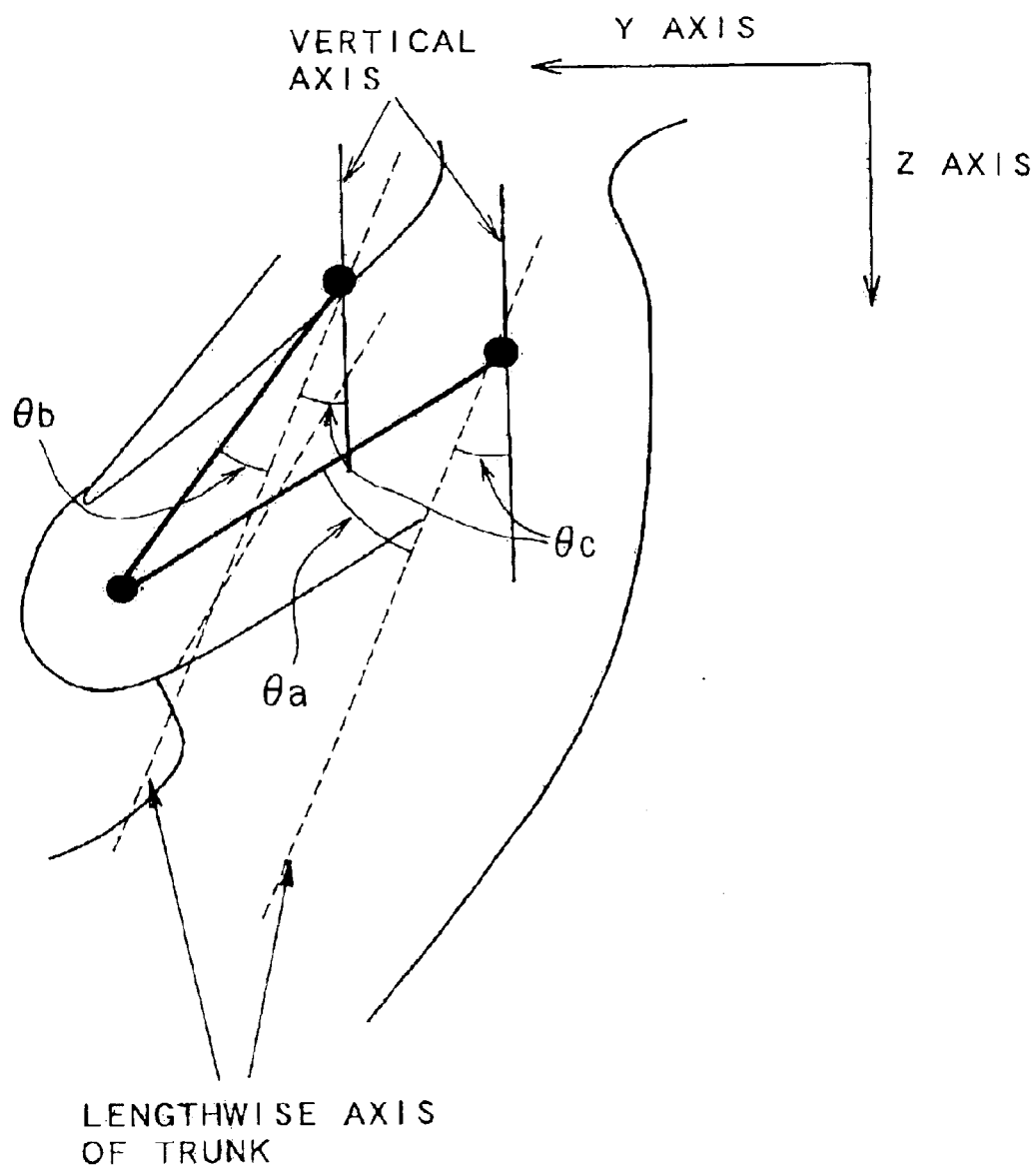
FIG. 22 illustrates how the electronic sphygmomanometer according to the embodiment calculates the difference ΔH between the altitudes of the cuff and the heart.

Here, how the electronic sphygmomanometer according to the embodiment described above calculates the difference ΔH in altitude between the cuff and the heart will be described in detail. As shown in FIGS. 21 and 22, if the angle of an upper arm in the left-and-right direction is referred to as Φa, the angle of the upper arm in the back-and-forth direction is referred to as θa, the angle of a forearm in the up-and-down direction is referred to as ϕb, the angle of the forearm in the back-and-forth direction is referred to as θb, the reclining angle of a body is referred to as θc, the forearm length is referred to as L1, the forearm length is referred to as L2, the altitude from a shoulder to the heart is referred to as H, and the altitude from the shoulder to the cuff is referred to as Z, the difference is expressed by the following basic equation.

$$\Delta H = Z - H = -L1^*\sin \phi b^*\cos(\theta b + \theta c) + L2^*\cos \phi a^*\cos(\theta a + \theta c) - H$$

However, with the method described in the "BACKGROUND OF THE INVENTION" section of this specification, the difference is expressed by the following estimated equation.

$$\Delta H = \alpha^* \sin \phi b + \beta (\alpha \text{ and } \beta \text{ are each a constant})$$

Therefore, there occur variations of estimation accuracy due to L1, L2, ϕa, θa, θb, and θc.

Here, with the electronic sphygmomanometer of this embodiment, if the angle in the vertical direction measured with the sphygmomanometer main body is referred to as ϕ1(ϕb=ϕ1), the angle in the back-and-forth direction measured with the sphygmomanometer main body is referred to as θ1(θb+θc=θ1), the angle in the left-and-right direction of the angle sensor placed on the upper arm of the upper arm is referred to as ϕ2(ϕa=ϕ2), the angle in the back-and-forth direction of the angle sensor placed on the upper arm of the upper arm is referred to as θ2(θa+θc=θ2), the manually inputted forearm length is referred to as L1, and the manually inputted upper arm length is referred to as L2, there is obtained the following equation.

$$\Delta H = -L1 * \sin\phi b * \cos(\theta b + \theta c) + L2 * \cos\phi a * \cos(\theta a + \theta c) - H$$

$$= -L1 * \sin\phi 1 * \cos\theta 1 + L2 * \cos\phi 2 * \cos\theta 2 - H$$

When the estimated equation is applied to subject persons whose statures are in a range of from 140 cm to 200 cm, it is possible to express the difference ΔH by the following equation.

$$\Delta H = -L1^*\sin \phi 1^*\cos \theta 1 + 0.957^* L2^*\cos \phi 2^*\cos \theta 2 - 1.1819$$

Here, +0.957 and 1.1819 are each a numeric value obtained as an approximate value of the parameter H through statistics.

As a result, the estimation accuracy concerning the altitude difference between the heart and the cuff of the sphygmomanometer is improved.

Figure 23:
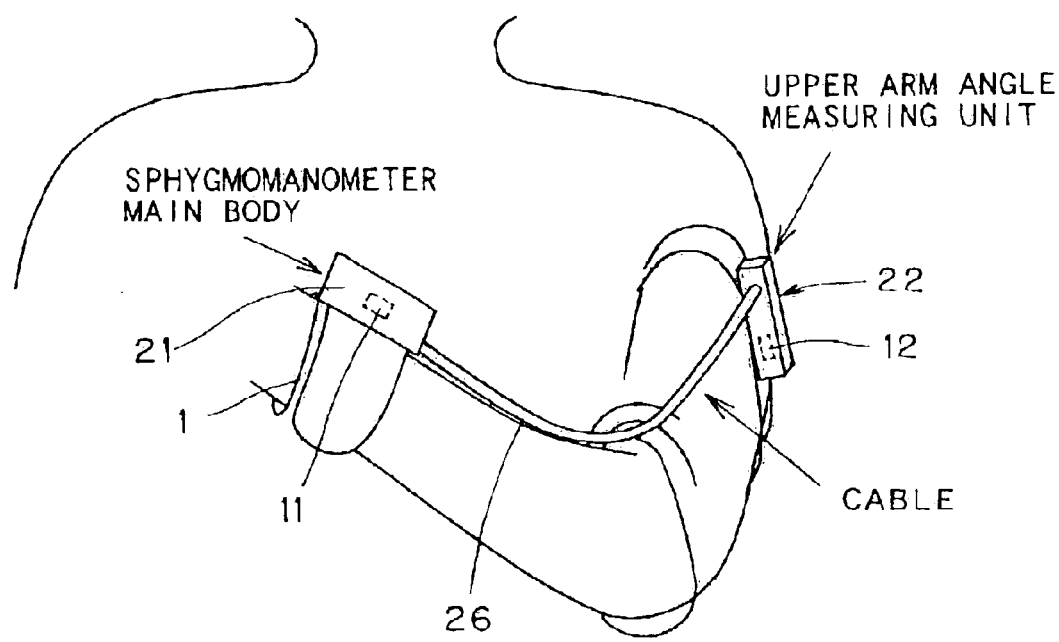
FIG. 23 is a perspective view showing the external appearance of an electronic sphygmomanometer according to the fifth embodiment of the present invention.

It should be noted here that in the electronic sphygmomanometer shown in FIG. 15 according to this embodiment, the sphygmomanometer main body 21 and the upper arm angle measuring unit 22 perform communications using infrared rays in a wireless manner. However, the communications may be performed using radio waves or data may be exchanged in a wired manner by connecting the sphygmomanometer main body 21 and the upper arm angle measuring unit 22 using a cable 26 as shown in FIG. 23.

(Fifth Embodiment)

An electronic sphygmomanometer according to the fifth embodiment of the present invention will be described below. This electronic sphygmomanometer has a construction that is the same as those of the electronic sphygmomanometers of the third and fourth embodiments. However, the present embodiment differs from the third and fourth embodiments in that the electronic sphygmomanometer does not include the upper arm angle measuring unit.

In this embodiment, using a biaxial angle detecting means provided for the main body of the electronic sphygmomanometer placed on a wrist, the measurement posture of a subject person, which is to say the difference in altitude between a heart and the pressure reference position of the sphygmomanometer, is calculated. Then, the determination as to the measurement posture or the correction of a blood pressure value is performed. Also, it is recommended that the electronic sphygmomanometer according to this embodiment is used to measure a blood pressure under a condition where there is maintained a posture shown in FIG. 24 in which a portion under the arm is closed and the forearm is held along the chest (when doing so, it is preferable that the elbow of an arm, on which the sphygmomanometer is placed, is supported using another hand so that the elbow does not depart from the body). The electronic sphygmomanometer main body 21 is attached so that the belt-like cuff 1 wound around the wrist is positioned with reference to the thumb side. Consequently, if the subject person takes the measurement posture shown in FIG. 24, the display unit 10 faces upward and it becomes easy for the subject person to confirm displayed contents.

Figure 25:
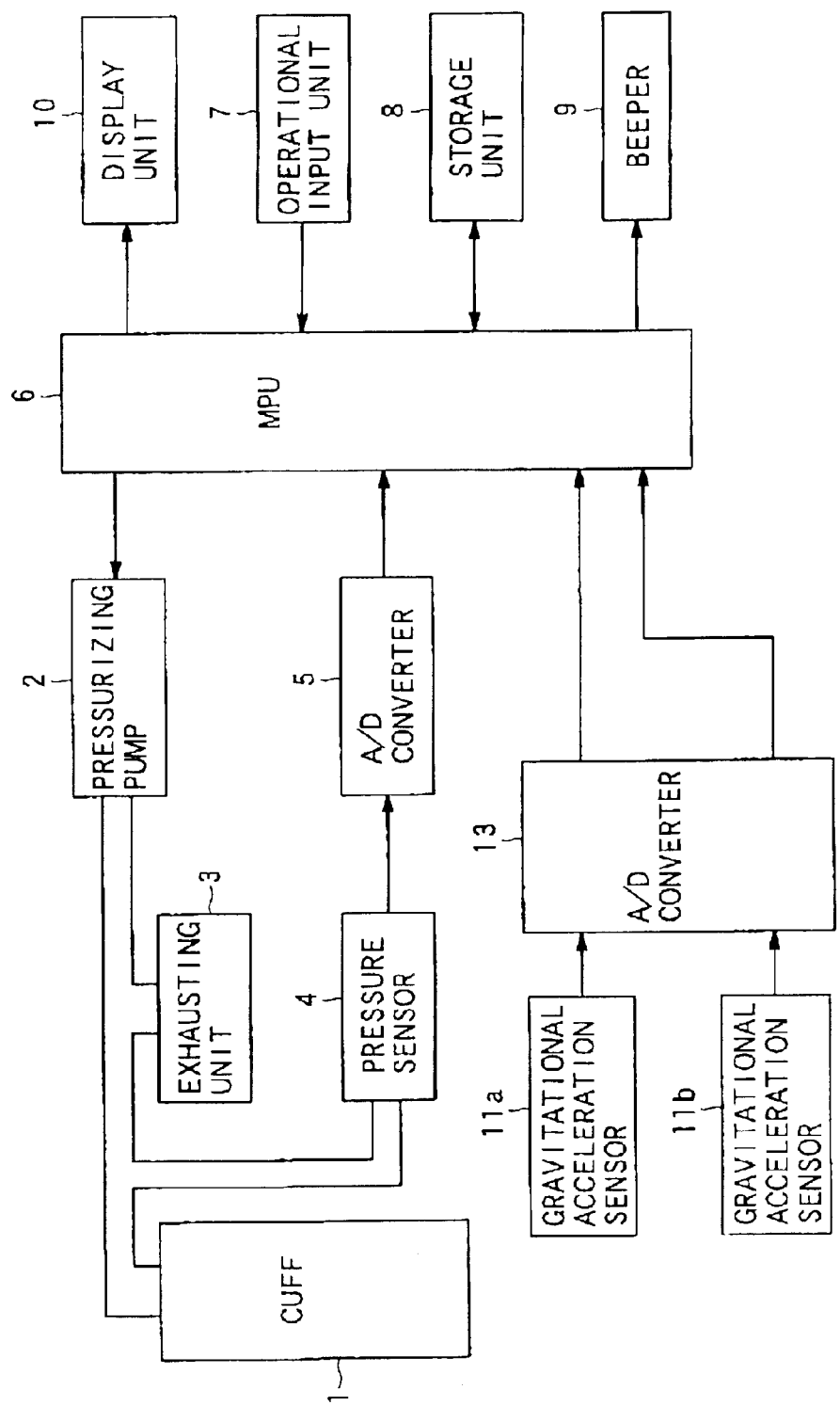
FIG. 25 is a block diagram showing the construction of the electronic sphygmomanometer according to the fifth embodiment.

FIG. 25 is a block diagram showing the construction of the electronic sphygmomanometer according to the fifth embodiment. The same constructions as in the first embodiment are given the same reference numerals and are not described in this embodiment.

Figure 26:
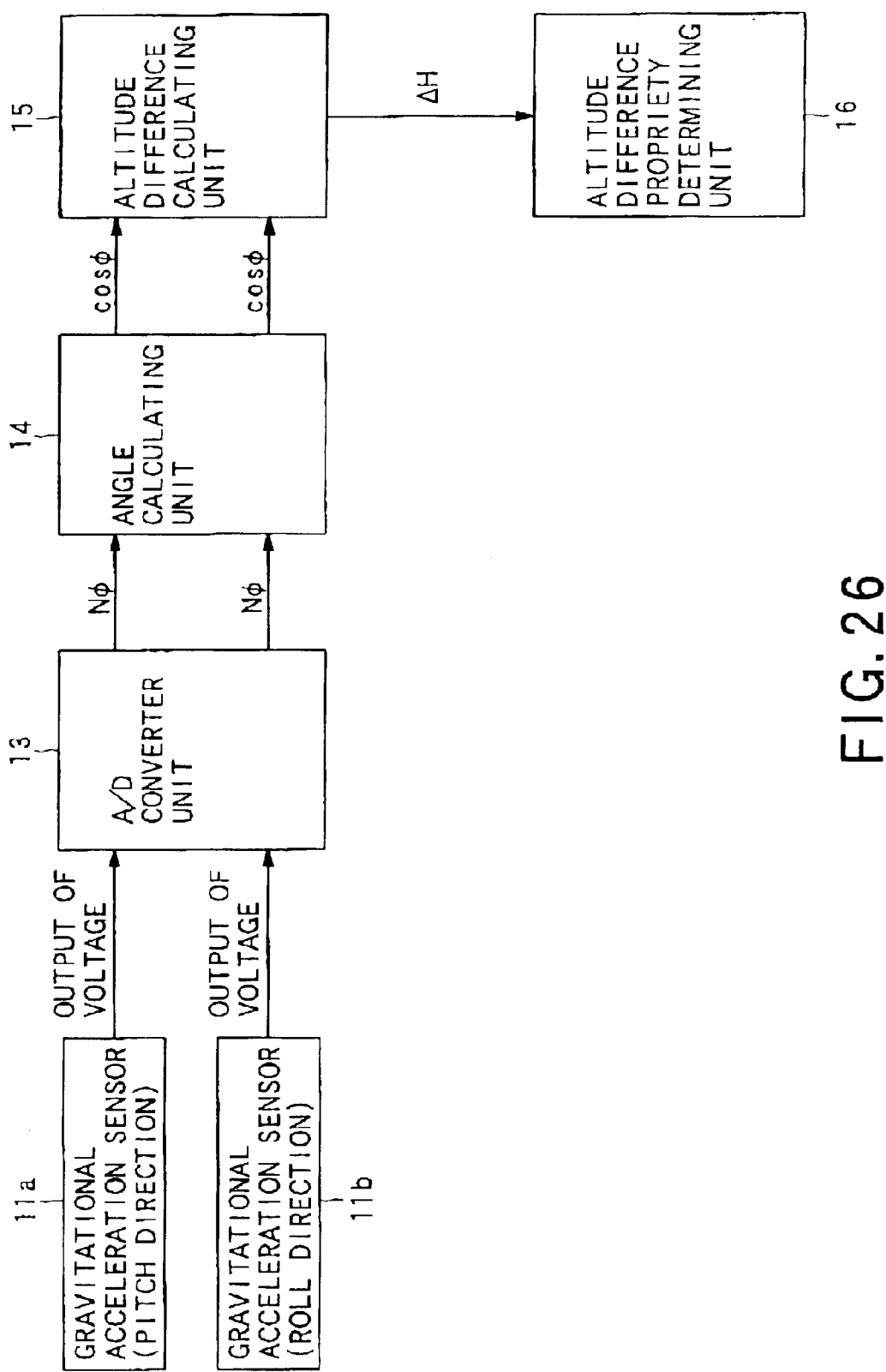
FIG. 26 is a functional block diagram of a main portion of the electronic sphygmomanometer according to the fifth embodiment.

FIG. 26 is a functional block diagram of a main portion of the electronic sphygmomanometer according to this embodiment. The function of each unit will be described below with reference to FIG. 26.

A gravitational acceleration sensor 11a in the pitch direction and a gravitational acceleration sensor 11b in the roll direction provided for the electronic sphygmomanometer placed on a wrist of a subject person output voltages corresponding to the gravitational accelerations in respective measurement directions.

The voltages outputted from the gravitational acceleration sensors 11a and 11b are inputted into the A/D converting unit 13. In the A/D converting unit 13, the analog values outputted from the gravitational acceleration sensors 11a and 11b are converted into digital values. The data converted into the digital values in the A/D converting unit 13 is inputted into the angle calculating unit 14.

In the angle calculating unit 14, digital values corresponding to specific gravitational acceleration states are stored in a predetermined storage area. The angle calculating unit 14 calculates angle information by comparing the stored values with the data inputted from the A/D converting unit 13. For instance, if a count value is referred to as $N\phi 0$ when the gravity acceleration in the pitch direction is 0G, the count value is referred to as $N\phi g$ when the gravity acceleration in the pitch direction is +1G, and the current count value of the gravitational acceleration in the pitch direction is referred to as $N\Phi$, it is possible to calculate angle information in the pitch direction using the following equation.

$$\cos \phi = (N\phi 0 - N\phi)/(N\phi 0 - N\phi g)$$

It is also possible to calculate angle information in the roll direction in the same manner.

Figure 27:
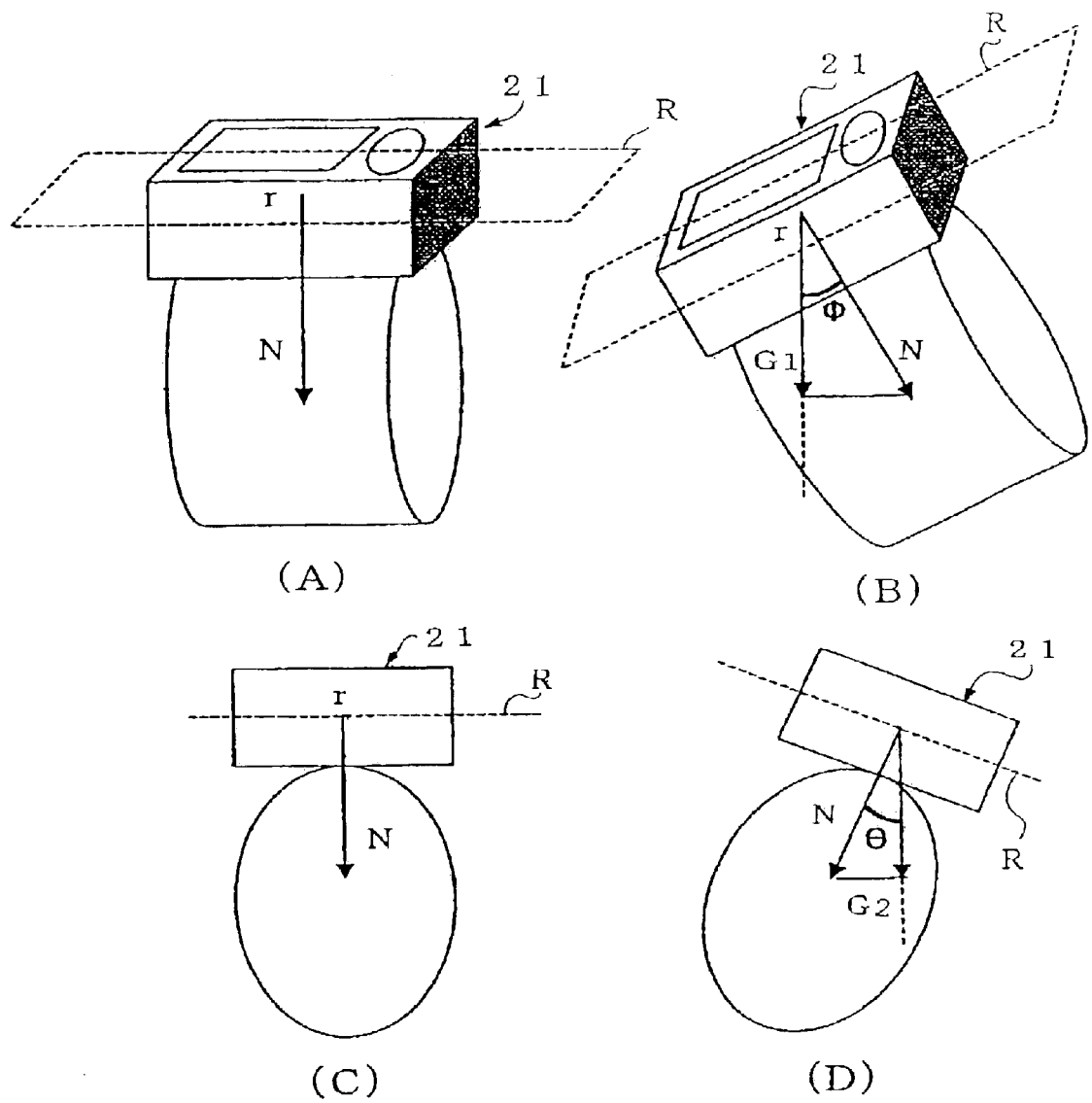
FIG. 27 illustrate measured angle information.

Here, angles obtained as the angle information on the basis of the gravitational acceleration sensors 11a and 11b will be described with reference to FIGS. 27. Here, a point "r" (hereinafter referred to as the "reference point") is set within the sphygmomanometer main body 21 attached to the cuff 1, thereby assuming a plane "R" (hereinafter referred to as the "reference plane") that passes through this reference point "r", extends parallel to the display surface of the sphygmomanometer main body 21 having an approximately cube shape, and is fixed to the sphygmomanometer main body 21. In this embodiment, an angle between the projective component G1 of a gravity acceleration vector to a plane that passes through the reference point "r", contains the normal line N (see FIG. 27A) extending perpendicular to this reference plane "R", and extends in the lengthwise direction of the sphygmomanometer main body 21 (coincides with the lengthwise direction of the forearm of the subject person) and the normal line N described above is defined as $\Phi$ (see FIG. 27B). Also, an angle between the projective component G2 of a gravity acceleration vector to a plane that passes through the reference point "r", contains the normal line N (see FIG. 27C) extending perpendicular to the reference plane "R", and extends in the widthwise direction of the sphygmomanometer main body 21 (coincides with the direction perpendicular to the lengthwise direction of the forearm of the subject person) and the normal line described above is defined as $\Theta$ (see FIG. 27D). The angles $\Phi$ and $\Theta$ described here are defined in accordance with the locations of the two gravitational acceleration sensors provided for the sphygmomanometer main body.

Figure 28:
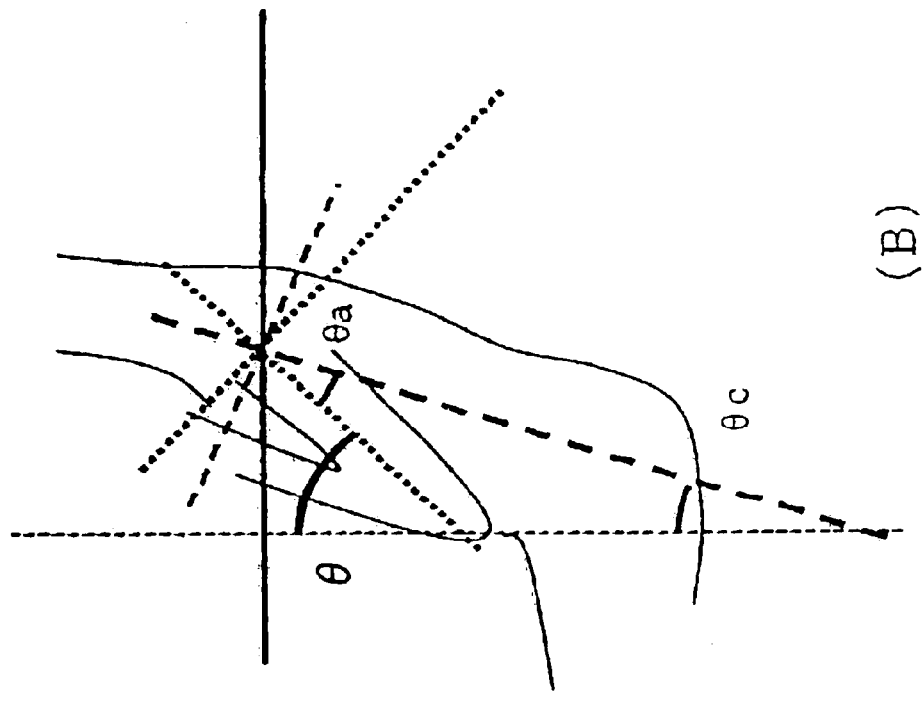
FIG. 28 illustrate angle variables used to calculate ΔH.
Figure 28:
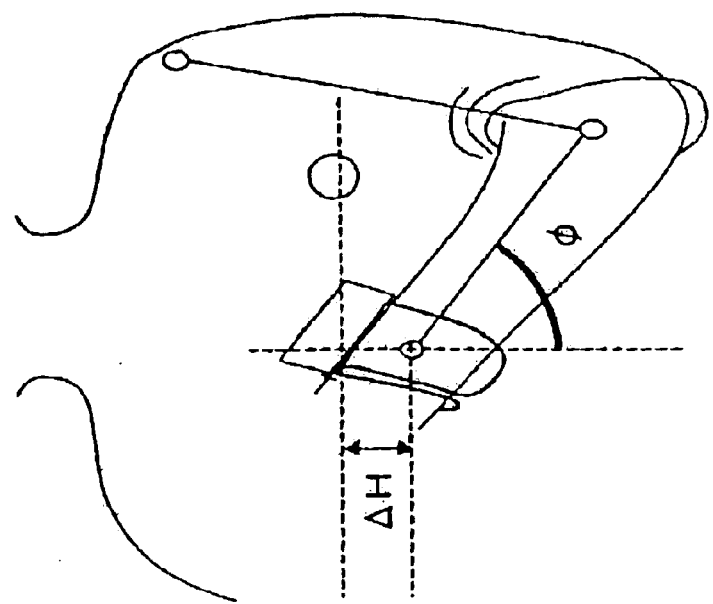

The calculated angle information is inputted into the altitude difference calculating unit 15. The altitude difference calculating unit 15 calculates an altitude difference between the heart and the pressure reference position of the sphygmomanometer from the calculated angels in the roll direction and the pitch direction. For instance, if an altitude difference between the heart and the pressure reference position of the sphygmomanometer in the vertical direction is referred to as $\Delta H$, the angle between the forearm and a vertical straight line is referred to as $\Phi$ (see FIG. 28A), the angle between the upper arm and the vertical straight line is referred to as $\theta$, the angle between the upper arm and the lengthwise direction of a trunk (for instance, there is assumed a line passing through the upper arm caput of the shoulder) is referred to as $\theta 2$, and the angle between the lengthwise direction of the trunk and the vertical direction is referred to as $\theta 1$ (see FIG. 28B), there is obtained the following equation.

$$\Delta H = L2^* \cos \phi a^* \cos(\theta a + \theta c) - L1^* \cos \phi_B^* \cos(\theta d + \theta c + \theta a) - H$$

Here, $\theta d$ is an angle between the lengthwise direction of the upper arm and the lengthwise direction of the forearm, and $\phi_B = 90° - \phi b$.

Here, if $\theta d = 0°$, there is obtained the following equation.

$$\Delta H = L2^* \cos \phi a^* \cos \theta - L1^* \cos \phi_B^* \cos \theta - H$$

Here, if variations in L1, L2, $\phi a$, and H are taken into account, it is possible to express the difference $\Delta H$ using the following equation.

$$\Delta H = A^* \cos \phi_B + B^* \cos \theta + C$$

Here, by substituting angle information $\Phi$ and $\Theta$ calculated on the basis of the measurement results of the gravitational acceleration sensors into $\phi$ and $\theta$, it becomes possible to calculate the difference between the heart and the pressure reference position of the sphygmomanometer using the angles detected by the biaxial angle detecting means. Note that this embodiment is based on the premise that measurement is performed under a condition where $\theta d$ is around 0° and the wrist is not twisted.

Figure 24:
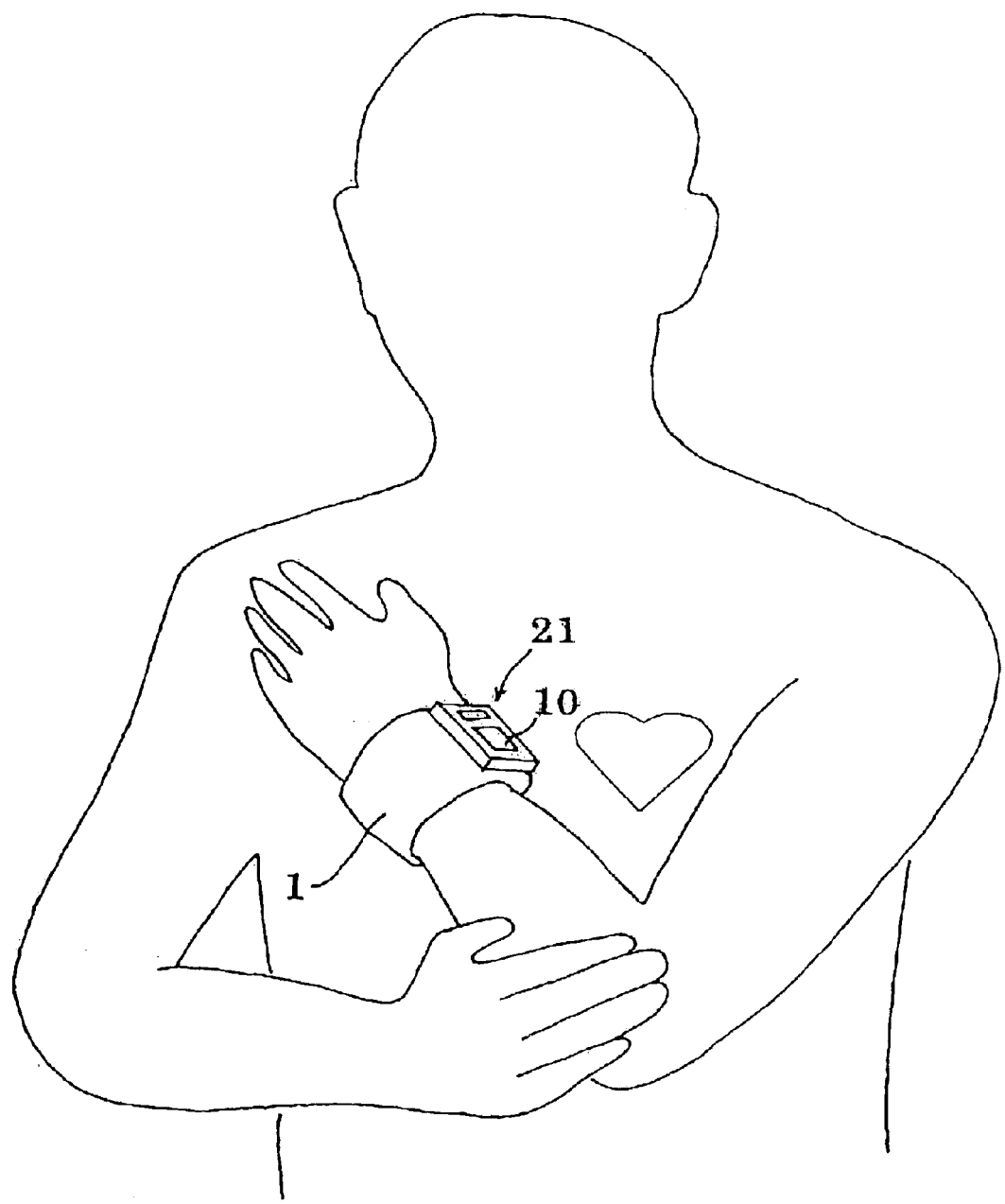
FIG. 24 shows a measurement posture when the electronic sphygmomanometer is used.

In this embodiment, the posture shown in FIG. 24 is maintained. As a result, it becomes possible to precisely calculate the difference between the heart and the pressure reference position of the sphygmomanometer using angles detected by two angle detecting means provided for the sphygmomanometer main body placed on the wrist without using a member that is used for positioning, such as a base or a pillow on which the elbow is placed. That is, the electronic sphygmomanometer according to this embodiment achieves the improvement in accuracy by paying attention to the structural feature of a human body that an error about the calculation of an altitude difference between the heart and the wrist, on which the sphygmomanometer is placed, depends on the degree of freedom of the elbow and shoulder. Also, the angle detecting means is used, so that it becomes possible to precisely calculate the difference between the heart and the pressure reference position of the sphygmomanometer even in the case where there exist error causing factors resulting from a posture, such as the reclining, of a subject person as well as the relative positional relation between a trunk and an arm.

The difference $\Delta H$ calculated by the altitude difference calculating unit 15 is inputted into the altitude difference propriety determining unit 16. The altitude difference propriety determining unit 16 determines whether the calculated $\Delta H$ exists within an appropriate range. Also, even if the calculated $\Delta H$ exists outside the appropriate range, a notification is issued to allow the subject person to recognize how degree the calculated $\Delta H$ deviates from the appropriate range in the manner to be described later.

Here, each function of the angle calculating unit 14, the altitude difference calculating unit 15, the altitude difference propriety determining unit 16, and the like is realized by the software processing of the MPU shown in FIG. 25.

Figure 29:
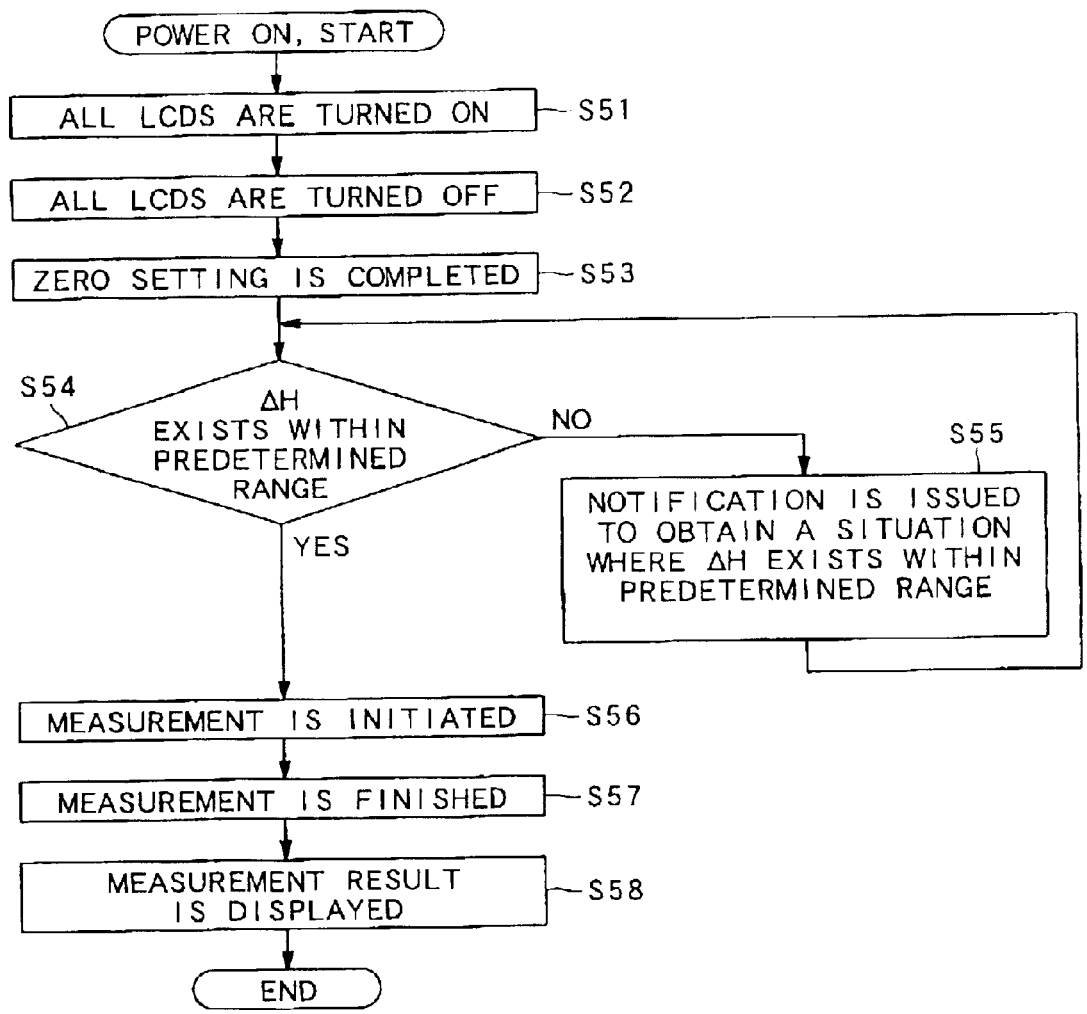
FIG. 29 is a flowchart showing a processing operation of the electronic sphygmomanometer according to the fifth embodiment.

Next, FIG. 29 is the flowchart which shows the processing operation of the electronic sphygmomanometer according to this embodiment.

When power is turned on and the operation is started, all of display devices of the display unit 10 are first turned on (step ST51). Following this, all of the display devices of the display unit are turned off (step ST52) to obtain a situation where it is possible to confirm the display function. Then, zero setting is completed (step ST53). Next, the MPU 6 calculates an altitude difference $\Delta H$ between the pressure reference position of the wrist and the heart of the subject person on the basis of the angle information of a forearm detected using the gravitational acceleration sensor 11a in the pitch direction and the gravitational acceleration sensor 11b in the roll direction and determines whether ΔH exists within a predetermined range (step ST54). If ΔH exists outside the predetermined range, a guiding notification is issued to obtain a situation where the altitude of the pressure reference position of the wrist of the subject person becomes the same as the altitude of the heart (step ST55).

Figure 30:
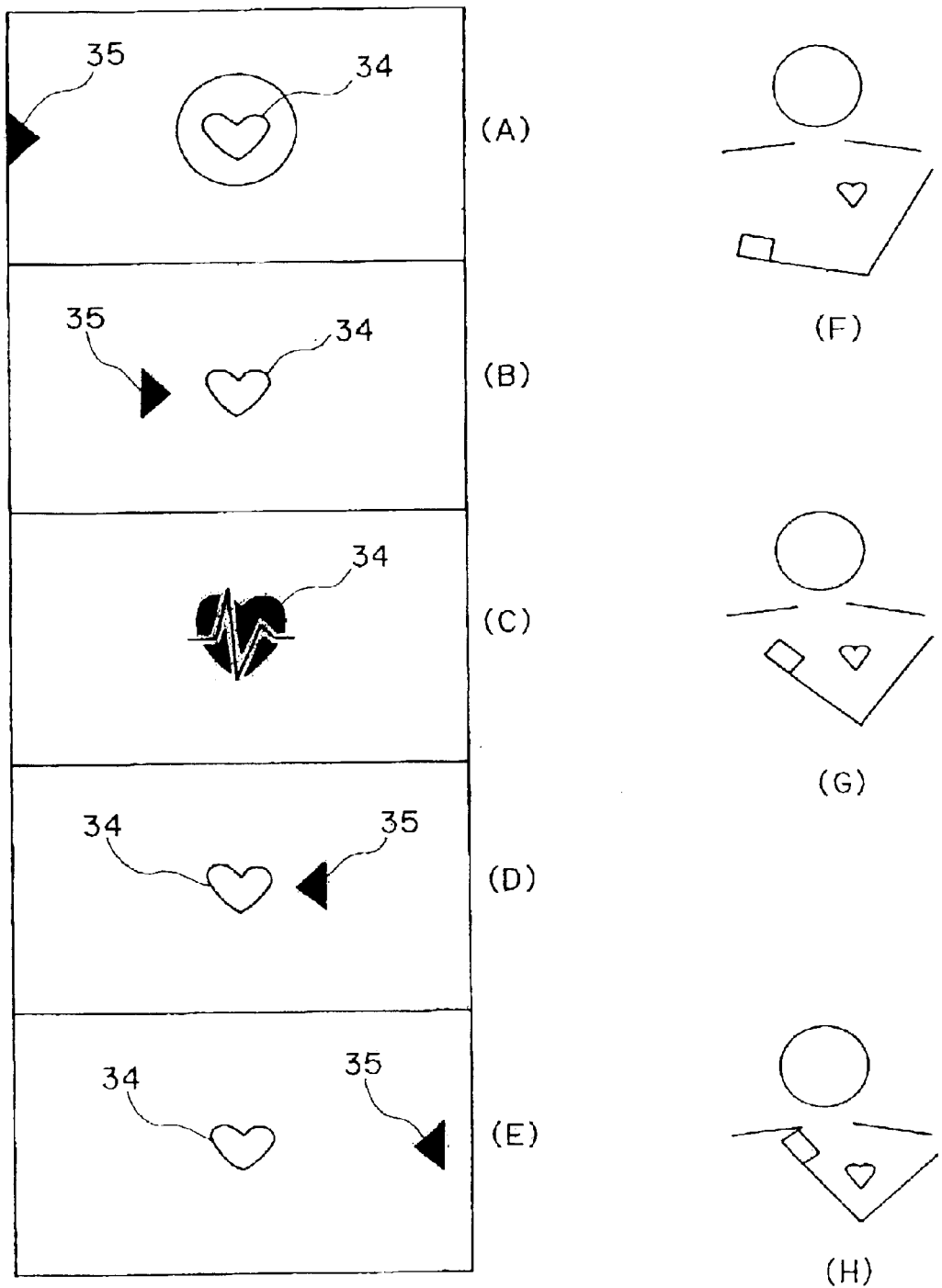
FIGS. 30A to 30H illustrate how the electronic sphygmomanometer according to the fifth embodiment notifies a measurement posture.

Here, the way how the electronic sphygmomanometer according to this embodiment notifies whether the altitude difference between the heart and the pressure reference position of the sphygmomanometer is proper or not will be described with reference to FIG. 30. FIGS. 30A to 30E each show an example of contents displayed on the display unit 10 to notify whether the altitude difference between the heart and the pressure reference position of the sphygmomanometer is proper or not. Each of FIGS. 30F to 30H shows a relation between the heart H and the pressure reference position of the sphygmomanometer 21 corresponding to the displayed contents shown on the left side of the drawing.

A heart mark 34 is displayed at the center of the display unit 10 as a target position. A triangle 35 directed toward the center of the display unit 10 moves in the left-and-right direction in accordance with the difference between the heart H and the pressure reference position of the sphygmomanometer 21. In the case where the pressure reference position of the sphygmomanometer 21 exists at a position that is lower than the heart as shown in FIG. 30F, the triangle 35 is positioned on the left side of the heart mark 34 as shown in FIG. 30A to notify the subject person that the position of the sphygmomanometer 21 exists outside the appropriate range. In accordance with the reduction of a distance between the sphygmomanometer 21 and the heart H, the triangle 35 moves rightward (FIG. 30B) to notify the subject person that the position of the sphygmomanometer 21 approaches an appropriate position. In the case where the altitude of the pressure reference position of the sphygmomanometer 21 becomes the same as the altitude of the heart as shown in FIG. 30G, the triangle 35 is superimposed on the heart mark 34. In this case, as shown in FIG. 30C, the shape of the heart mark 34 is changed so that a pulsatory motion is superimposed on a heart. In this manner, the subject person is notified that the pressure reference position of the sphygmomanometer 21 exists within an appropriate range in which the altitude of the pressure reference position becomes almost the same as the altitude of the heart. In this case, the beeper is turned on to allow the subject person to easily recognize that the sphygmomanometer 21 exists within the appropriate range. If the position of the sphygmomanometer 21 is raised, the triangle 35 is changed so as to be directed leftward and is displayed on the right side of the heart mark 34 (see FIG. 30D), thereby notifying the subject person that the position of the sphygmomanometer 21 is departing from the appropriate position. When the position of the sphygmomanometer is further raised, the triangle 35 further moves rightward with reference to the heart mark 34 (see FIG. 30E), thereby notifying the subject person that the position of the sphygmomanometer 21 exists outside the appropriate range.

In step ST54, when the altitude difference between the heart and the pressure reference position of the electronic sphygmomanometer placed on the wrist of the subject person exists within the predetermined range or enters into the predetermined range, the MPU 6 turns on the pressuring pump 2 and issues an instruction to initiate measurement (step ST56). When the measurement of the highest blood pressure, the lowest blood pressure, and the pulse rate is finished (step ST57), measurement results are displayed (step ST58) and the operation is finished.

As described above, it is notified whether the position of the sphygmomanometer 21 exists within an appropriate range using the position of the mark 35 that moves in the left-and-right direction on the display unit 10, so that there is prevented a situation where the subject person needs to adjust his/her measurement posture again because he/she separates an arm, on which the sphygmomanometer 21 is placed, from his/her body in accordance with the movement of the mark during the adjustment of the position of the sphygmomanometer 21. This makes it possible to efficiently perform the positional adjustment and to initiate the measurement without consuming a long time period.

The gravitational acceleration sensors are used to calculate angles in this embodiment, although the means for detecting the angles is not limited to these sensors.

(Sixth Embodiment)

Figure 31:
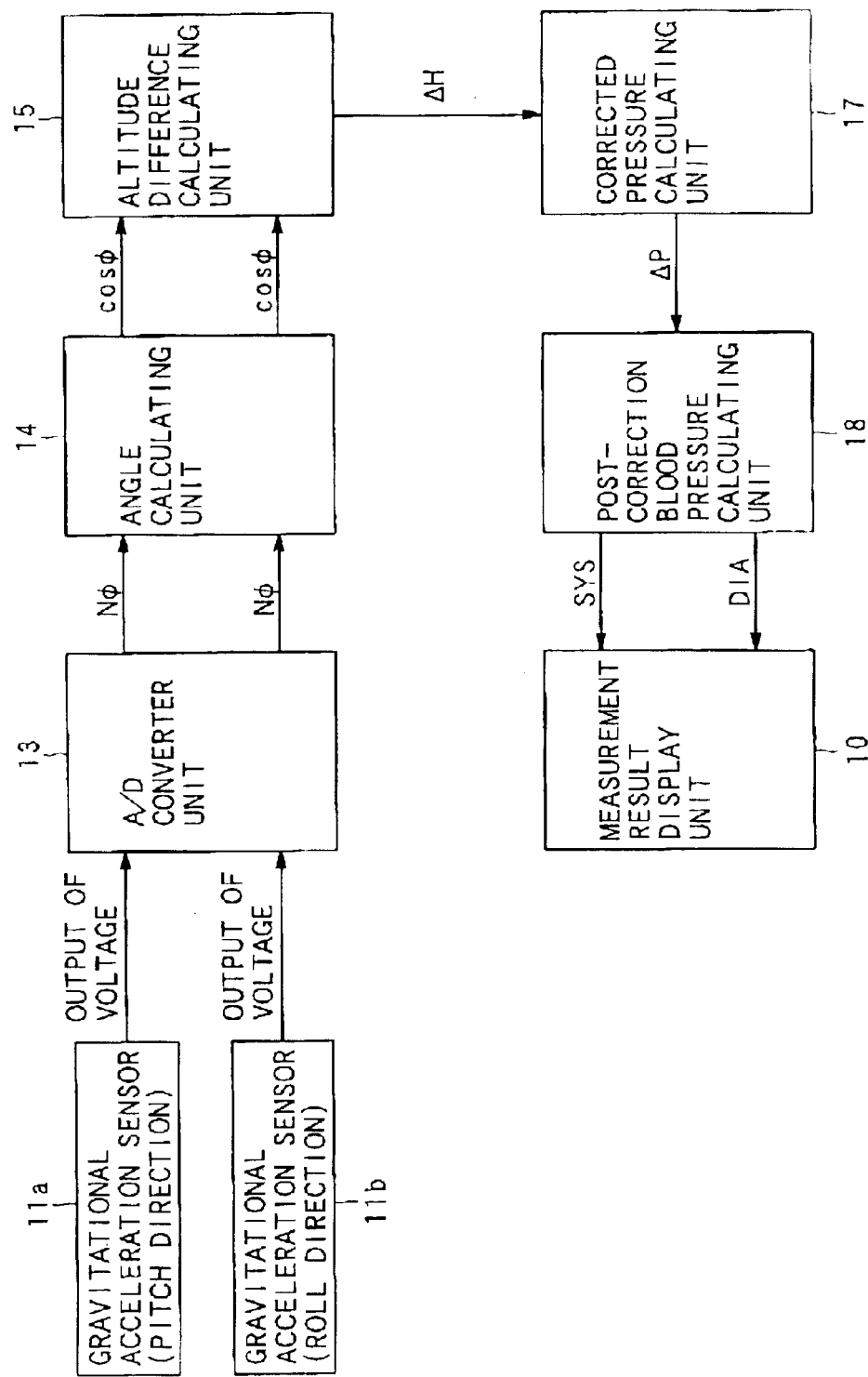
FIG. 31 is a functional block diagram of a main portion of an electronic sphygmomanometer according to the sixth embodiment.
Figure 32:
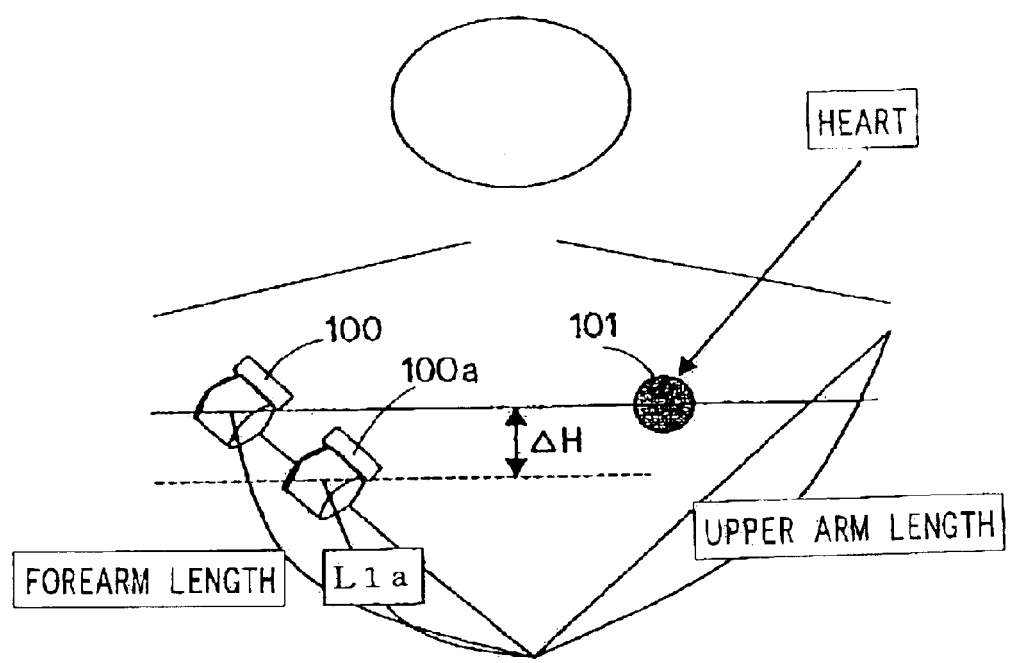
FIG. 32 illustrates how the altitude of a main body is changed by a difference between forearm lengths even if the same pitch angle is maintained.
Figure 33:
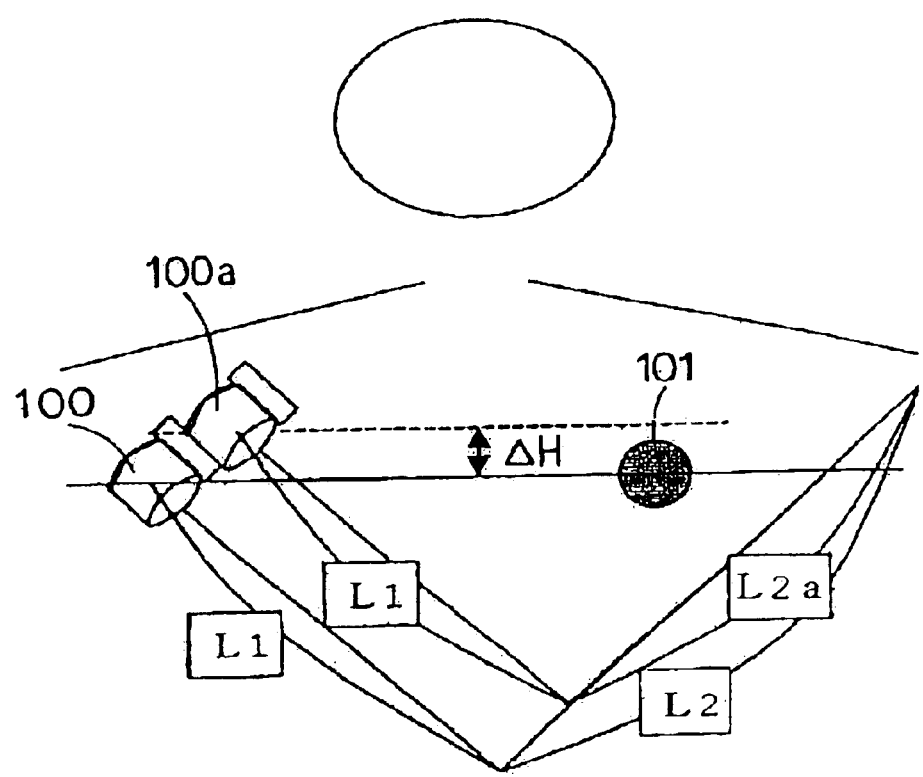
FIG. 33 illustrates how the altitude of the main body is changed by a difference between upper arm lengths even if the same pitch angle is maintained.
Figure 34:
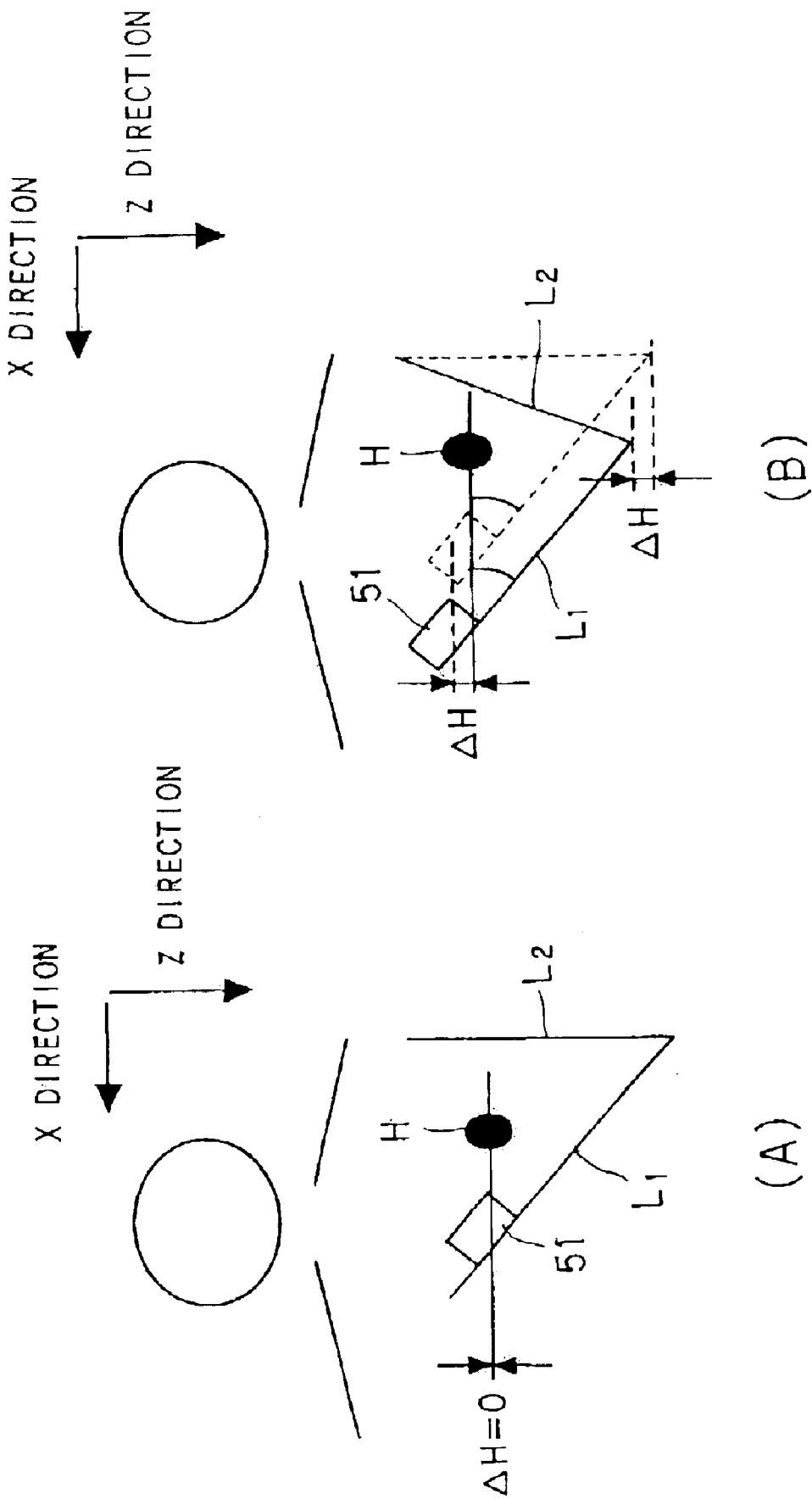
FIGS. 34A and 34B illustrate a problem caused in the case where the upper arm of a subject person is inclined in the pitch direction.
Figure 35:
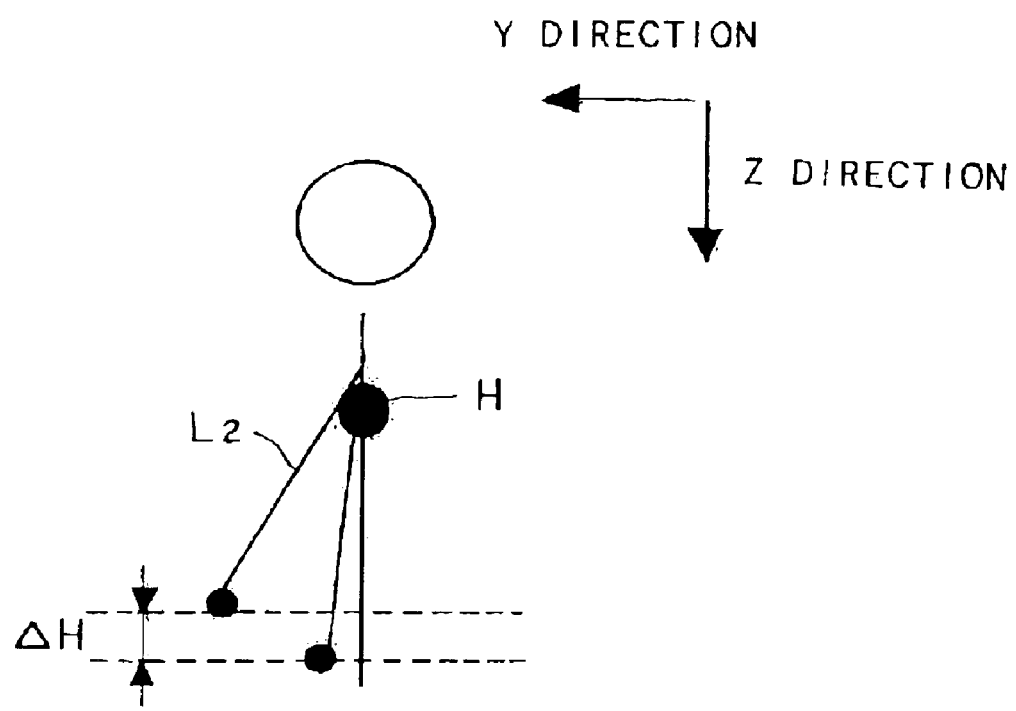
FIG. 35 illustrates a problem caused in the case where the upper arm is inclined in the roll direction.
Figure 36:
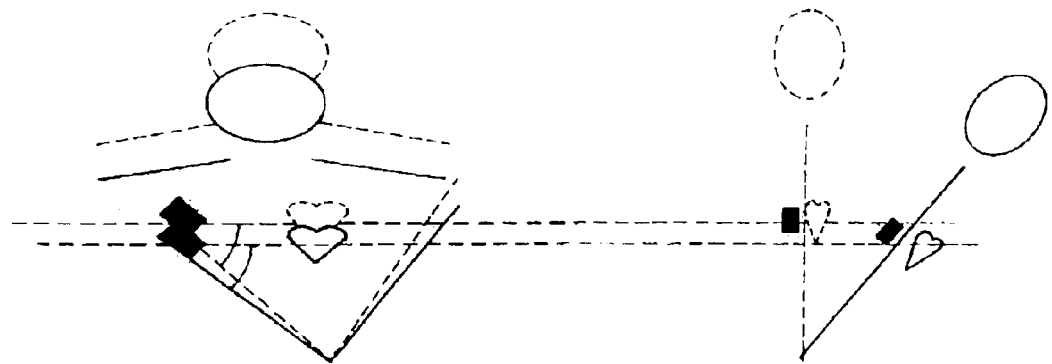
FIG. 36 illustrates a problem caused in the case where the body of the subject person is inclined.
Figure 37:
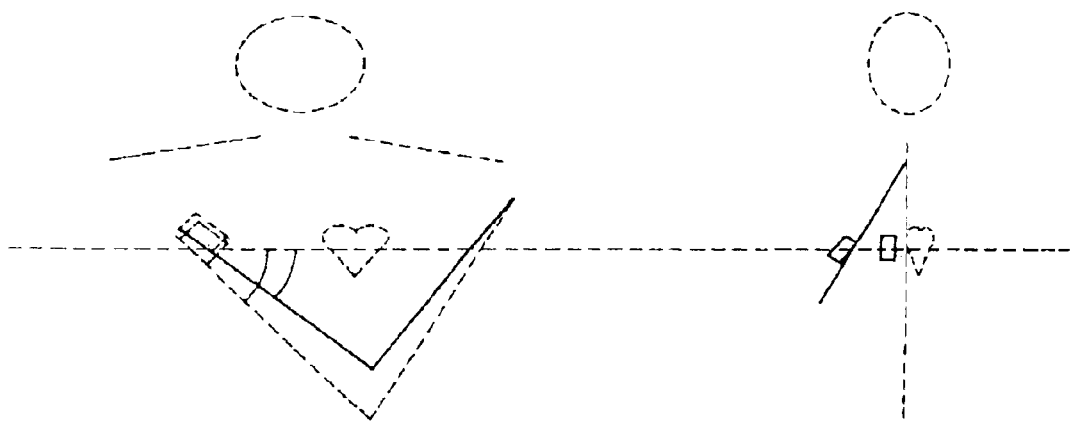
FIG. 37 illustrates a problem caused in the case where the forearm of the subject person is inclined.

FIG. 31 is a functional block diagram of the main portion of an electronic sphygmomanometer according to the sixth embodiment. The overall construction of the electronic sphygmomanometer 21 is the same as that in the fifth embodiment shown in FIG. 25. The same constructions are given the same reference numerals and are not described in this embodiment.

The construction of each of the gravitational acceleration sensors 11a and 11b, the A/D converting unit 13, the angle calculating unit 14, and the altitude difference calculating unit 15 is the same as that in the fifth embodiment shown in FIG. 26. Therefore, the construction is not described in this embodiment.

In this embodiment, the difference ΔH calculated by the altitude difference calculating unit 15 is inputted into the corrected pressure calculating unit 17. The corrected pressure calculating unit 17 calculates a corrected pressure on the basis of a calculated altitude difference between the heart and the pressure reference position of the sphygmomanometer 21. For instance, if the corrected pressure is referred to as ΔP, it is possible to calculate the corrected pressure using the following equation.

$$\Delta P = \Delta H * 7.8/10$$

The corrected pressure calculated by the corrected pressure calculating unit 17 is inputted into a post-correction blood pressure calculating unit 18. The post-correction blood pressure calculating unit 18 calculates a post-correction blood pressure by adding ΔP to SYS' (pre-correction highest blood pressure) and DIA' (pre-correction lowest blood pressure) obtained by the measurement by the sphygmomanometer. That is, if the post-correction highest blood pressure and the post-correction lowest blood pressure are respectively referred to as SYS and DIA, post-correction blood pressure values are calculated from the following equations.

$$SYS = SYS' + \Delta P$$

$$DIA = DIA' + \Delta P$$

The values SYS and DIA calculated in this manner are displayed by the display unit 10 as measurement results.

Here, the function of each of the angle calculating unit 14, the altitude difference calculating unit 15, the corrected pressure calculating unit 17, the post-correction blood pressure calculating unit 18, and the like is realized by the software processing of the MPU 6 shown in FIG. 25.

INDUSTRIAL APPLICABILITY

With the technique of the present invention, a posture detecting means is constructed using an altitude detecting means for detecting the altitude of a measurement region and a living body information inputting means for inputting living body information of a subject person. Whether measurement is proper or not or whether a posture is proper or not is measured using a posture detected by this posture detecting means. Alternatively, a measured blood pressure value is corrected using an output from the posture detecting means. This makes it possible to reduce the degradation of the accuracy of the altitude measurement due to variations in upper arm length, forearm length, and the like among subject persons. As a result, it becomes possible to more precisely measure a blood pressure.

With the technique of the present invention, aside from a sphygmomanometer main body, there is provided an upper arm angle detector. An upper arm angle detected by this upper arm angle detector is also reflected in the calculation of a difference value between the altitudes of a heart and a cuff. This makes it possible to precisely calculate a difference value between the altitude of the cuff of the sphygmomanometer and the altitude of a heart regardless of a measurement posture. As a result, it becomes possible to precisely measure a blood pressure while maintaining a high degree of freedom for the measurement posture.

With the technique of the present invention, it is possible to calculate an altitude difference between a heart and a predetermined reference position of a sphygmomanometer in the vertical direction on the basis of angles of two axes and to exactly determine the measurement posture of a subject person. This eliminates the necessity to use another positioning member or the like. As a result, it becomes possible to precisely measure a blood pressure without difficulty while maintaining a high degree of freedom for the measurement posture.

Also, with the technique of the present invention, an altitude difference between a heart and a predetermined reference position of a sphygmomanometer in the vertical direction is calculated on the basis of angles of two axes and a blood pressure value is corrected on the basis of this altitude difference. As a result, it becomes possible to more precisely measure a blood pressure.

What is claimed is:

1. An electronic sphygmomanometer comprising:
a measuring unit that is placed on a predetermined region and measures one of a blood pressure and hemodynamics;
a posture detecting unit to detect a posture of a subject person;
a propriety determining unit to determine whether the measurement using the posture detected by the posture detecting unit is proper or not; and
a notifying unit to notify a result of the determination by the propriety determining means unit,
wherein the posture detecting unit includes: a living body information inputting unit to input living body information of the subject person; and an altitude detecting unit for detecting an altitude of a measurement region based on the living body information.

2. An electronic sphygmomanometer comprising:
a measuring unit that is placed on a predetermined region and measures one of a blood pressure and hemodynamics;
a posture detecting unit to detect a posture of a subject person;
a blood pressure value correcting unit to correct a blood pressure value measured by the measuring unit in accordance with the detected posture; and
a display unit to display the corrected blood pressure value,
wherein the posture detecting unit includes:
altitude detecting unit to detect an altitude of a measurement region; and living body information inputting unit to input living body information of the subject person.

3. An electronic sphygmomanometer comprising:
a measuring unit that is placed on a predetermined region and measures one of a blood pressure and hemodynamics;
a posture detecting unit to detect a posture of a subject person;
a propriety determining unit to determine whether the measurement using the posture detected by the posture detecting unit is proper or not; and
a notifying unit to notify a result of the determination by the propriety determining unit;
wherein the posture detecting unit includes:
altitude detecting unit to detect one of an inclination angle with respect to an axis and inclination angles with respect to two axes and detecting an altitude of a measurement region using the detected inclination angle or angles; and
a living body information inputting unit to input living body information concerning the subject person.

4. An electronic sphygmomanometer comprising:
a measuring unit that is placed on a predetermined region and measures one of a blood pressure and hemodynamics;
a posture detecting unit to detect a posture of a subject person;
a blood pressure value correcting unit to correct a blood pressure value measured by the measuring unit in accordance with the detected posture; and
a display unit to display the corrected blood pressure value, wherein the posture detecting unit includes:
altitude detecting unit to detect one of an inclination angle with respect to an axis and inclination angles with respect to two axes and detecting an altitude of a measurement region using the detected inclination angle or angles; and
living body information inputting unit to input living body information concerning the subject person.

5. An electronic sphygmomanometer according to claim 3 or 4,
wherein the directions of the two axes are a roll direction and a pitch direction of a wrist.

6. An electronic sphygmomanometer according to claim 3 or 4,
wherein the directions of the two axes are a pitch direction of a wrist and an inclination of a body.

7. An electronic sphygmomanometer according to claim 1, 2, 3, or 4,
wherein the living body information inputting unit includes a length information inputting unit to input at least one of a forearm length and an upper arm length.

8. An electronic sphygmomanometer according to claim 1, 2, 3, or 4,
wherein the living body information inputting unit includes a stature information inputting unit to input a stature.

9. An electronic sphygmomanometer comprising:
a measuring unit that is placed on a predetermined region and measures one of a blood pressure and hemodynamics;

a posture detecting unit to detect a posture of a subject person;

a propriety determining unit to determine whether the measurement on the basis of the posture detected by the posture detecting means unit is proper or not;

a notifying unit to notify a result of the determination by the propriety determining means unit; and wherein the posturing detecting unit is separated from a main body of the sphygmomanometer and detects at least one upper arm angle.

10. An electronic sphygmomanometer comprising:

a measuring unit that is placed on a predetermined region and measures one of a blood pressure and hemodynamics;

a posture detecting unit to detect a posture of a subject person;

blood pressure value correcting unit to perform calculation on a blood pressure value measured by the measuring unit using a correction value in accordance with the posture detected by the posture detecting unit;

a display unit to display the blood pressure value corrected by the blood pressure value correcting unit; and a unit that is separated from a main body of the sphygmomanometer and detects at least one upper arm angle.

11. An electronic sphygmomanometer according to claim 9, wherein the unit that detects at least one angle is placed on an upper arm.

12. An electronic sphygmomanometer according to claim 9, wherein the electronic sphygmomanometer and the unit that detects at least one upper arm angle are constructed so as to be capable of exchanging data using communications means.

13. An electronic sphygmomanometer according to claim 9, 10, 11, or 12, further comprising living body information inputting unit.

14. An electronic sphygmomanometer according to claim 9, 10, 11, or 12, wherein the unit that detects at least one upper arm angle is one of a uniaxial sensor and a biaxial sensor.

15. An electronic sphygmomanometer according to claim 14, wherein if the unit that detects at least one angle is the biaxial sensor, one axis exists on a vertical plane extending in a left-and-right direction of a body of the subject person and another axis exists on a vertical plane extending in a back-and-forth direction of the body of the subject person.

16. An electronic sphygmomanometer according to claim 14, wherein if the unit that detects at least one angle is the biaxial sensor, one axis exists on a vertical plane extending in a left-and-right direction of a body of the subject person and another axis exists on a horizontal plane extending in a back-and-forth direction of the body of the subject person.

17. An electronic sphygmomanometer comprising: a measuring unit that is placed on a predetermined region and measures one of a blood pressure and hemodynamics;

a biaxial angle detecting unit to detect angles of two axes;

a measurement posture altitude difference calculating unit to calculate an altitude difference in a vertical direction between a heart of a subject person and a predetermined reference position of the sphygmomanometer using the angles detected by the biaxial angle detecting unit;

a measurement posture propriety determining unit to determine whether the calculated altitude difference exists within a predetermined altitude difference range using a result of the calculation by the measurement posture altitude difference calculating unit; and a notifying unit to notify the subject person of a result of the determination by the measurement posture propriety determining unit.

18. An electronic sphygmomanometer comprising;

a measuring unit that is placed on a predetermined region and measures one of a blood pressure and hemodynamics;

a biaxial angle detecting means for detecting angles of two axes;

a measurement posture altitude difference calculating unit to calculate an altitude difference in a vertical direction between a heart of a subject person and a predetermined reference position of the sphygmomanometer using the angles detected by the biaxial angle detecting unit;

a correction pressure calculating unit to calculate a correction value for a blood pressure using a result of the calculation by the measurement posture altitude difference calculating unit;

a post-correction blood pressure calculating unit to calculate a post-correction blood pressure value using the correction value calculated by the correction pressure calculating unit and a blood pressure value measured by the measuring unit; and a measurement result notifying unit to notify the subject person of a result of the calculation by the post-correction blood pressure calculating unit.

19. An electronic sphygmomanometer according to claim 17 or 18, wherein the angles of two axes are an angle in a pitch direction and an angle in a roll direction when the electronic sphygmomanometer is placed on a forearm.

20. An electronic sphygmomanometer according to claim 18, wherein the measurement posture altitude difference calculating unit calculates an altitude difference of a measurement posture by setting the angle in the pitch direction as an angle of the forearm with reference to a horizontal plane and setting the angle in the roll direction as an angle obtained by combining an inclination angle of a body with reference to a vertical direction and an angle of an upper arm with reference to a lengthwise direction of a trunk.

* * * * *